(12) United States Patent
Tsunoda et al.

(10) Patent No.: US 8,298,816 B2
(45) Date of Patent: Oct. 30, 2012

(54) EXPRESSION SYSTEMS USING MAMMALIAN BETA-ACTIN PROMOTER

(75) Inventors: Hiroyuki Tsunoda, Ibaraki (JP); Kiyoshi Habu, Ibaraki (JP)

(73) Assignee: Chugai Seiyaku Kabushiki Kaisha, Tokyo (JP)

(*) Notice: Subject to any disclaimer, the term of this patent is extended or adjusted under 35 U.S.C. 154(b) by 608 days.

(21) Appl. No.: 10/581,183

(22) PCT Filed: Dec. 3, 2004

(86) PCT No.: PCT/JP2004/018006
§ 371 (c)(1), (2), (4) Date: May 18, 2007

(87) PCT Pub. No.: WO2005/054467
PCT Pub. Date: Jun. 16, 2005

(65) Prior Publication Data
US 2008/0250514 A1    Oct. 9, 2008

(30) Foreign Application Priority Data
Dec. 3, 2003 (JP) ................... 2003-405269

(51) Int. Cl.
*C12N 15/00* (2006.01)
*C12N 5/00* (2006.01)
*C12P 21/06* (2006.01)

(52) U.S. Cl. ............... 435/320.1; 435/69.1; 435/325; 435/455

(58) Field of Classification Search ............. None
See application file for complete search history.

(56) References Cited

U.S. PATENT DOCUMENTS

| | | | |
|---|---|---|---|
| 5,795,965 A | 8/1998 | Tsuchiya et al. | |
| 5,811,260 A | 9/1998 | Miyazaki et al. | |
| 6,468,798 B1* | 10/2002 | Debs et al. ............... | 435/458 |
| 6,689,583 B1 | 2/2004 | Jenuwein et al. | |
| 7,252,968 B2 | 8/2007 | Jenuwein et al. | |
| 7,423,135 B2* | 9/2008 | Estes et al. ............... | 536/23.1 |
| 2003/0072938 A1 | 4/2003 | Kappes et al. | |
| 2003/0224477 A1 | 12/2003 | Heartlein et al. | |

FOREIGN PATENT DOCUMENTS

| | | |
|---|---|---|
| DE | 195 16 776 | 11/1996 |
| JP | 7-502510 | 3/1995 |
| JP | H10-503372 | 3/1998 |
| JP | 2007-525956 | 9/2007 |
| WO | WO 92/19759 | 11/1992 |
| WO | WO 93/12240 | 6/1993 |
| WO | WO 96/04394 | 2/1996 |
| WO | WO 96/35784 | 11/1996 |
| WO | WO 00/15764 | 3/2000 |
| WO | WO 02/024932 | 3/2002 |
| WO | WO 02/102417 | 12/2002 |
| WO | WO 03/080648 | 10/2003 |
| WO | WO 03/092612 | 11/2003 |
| WO | WO 03/093479 | 11/2003 |
| WO | WO 2004/031357 | 4/2004 |
| WO | WO 2005/000888 | 1/2005 |

OTHER PUBLICATIONS

Klein et al. Methods 28:286-292; 2002.*
Beddington et al. Dev. 106:37-46; 1989.*
Hadjantonakis et al. Mech. Develop. 76:79-90, 1998.*
Yano et al. Cytotech. 16:167-178; 1994.*
GenBank BC011083 1-3, 2002.*
GenBank Accession No. NT_081055.1 dated Oct. 30, 2003, 3 pages.
GenBank Accession No. AF192534 dated Apr. 19, 2000, 3 pages.
GenBank Accession No. 704514.1 dated Aug. 3, 1993, 3 pages.
Kang et al., "Long-term expression of a T-cell receptor β-chain gene in mice reconstituted with retrovirus-infected hematopoietic stem cells," *Proc. Natl. Acad. Sci. USA*, 1990, 87:9803-9807.
Mason et al., "Expression of human bone morphogenic protein 7 in primary rabbit periosteal cells: potential utility in gene therapy for osteochondral repair," *Gene Therapy*, 1998, 5:1098-1104.
Antonucci et al., "Eukaryotic Promoters Drive Gene Expression in *Escherichia coil*," *J. Biol. Chem.*, 264:17656-17659 (1989).
Donis et al., "Comparison of Expression of a Series of Mammalian Vector Promoters in the Neuronal Cell Lines PC12 and HT4,"*BioTechniques*, 15:786-787 (1993).
Jaffe et al., "Developmental failure of chimeiic embryos expressing high levels of H-2D⁴ transplantation antigens," *Proc. Natl. Acad. Sci. USA*, 89:5927-5931 (1992).
Kim et al., "Gene transfer into bovine cells and embryos using rep-lication-defective retroviral vectors encapsidated with xenotropic murine leukemia virus envelopes," *Animal Biotechnology*, 4:53-69 (1993).
Kobayashi et al., "The CMV Enhancer Stimulates Expression of Foreign Genes from the Human EF-1αPromoter," *Anal. Biochem.*, 247:179-181 (1997).
Morgenstern et al., "A series of mammalian expression vectors and characterization of their expression of a reporter gene in stably and transiently transfected cells," *Nucleic Acids Res.*, 18:1068 (1990).
Niwa et al., "Efficient selection for high-expression transfectants with a novel eukaryotic vector," *Gene*, 108:193-200 (1991).
Nudel et al., "The nucleotide sequence of the rat cytoplasmic β-actin gene," *Nucleic Acids Res.*, 11:1759-1771 (1983).
Ramírez-Solís et al., "New vectors for the efficient expression of mammalian genes in cultured cells," *Gene*, 87:291-294 (1990).
Takebe et al., "SRα Promoter: an Efficient and Versatile Mammalian cDNA Expression System Composed of the Simian Virus 40 Early Promoter and the R-U5 Segment of Human T-Cell Leukemia Virus Type 1 Long Terminal Repeat," *Mol. Cell. Biol.*, 8:466-472 (1988).

(Continued)

*Primary Examiner* — Sumesh Kaushal
(74) *Attorney, Agent, or Firm* — Fish & Richardson P.C.

(57) ABSTRACT

Promoter activities were examined by comparing combinations of promoters and enhancers derived from various genes. A hybrid promoter comprising a combination of a CMV enhancer and a mammalian β-actin promoter, or the post-transcriptional regulatory region of the genomic sequence Woodchuck Hepatitis Virus (WPRE) and a mammalian β-actin promoter was found to be stronger than existing promoters. Furthermore, the activities of the β-actin promoters could be enhanced by coexpressing the oncogene product Ras, which is a transactivator.

34 Claims, 4 Drawing Sheets

OTHER PUBLICATIONS

Xu et al., "Optimization of transcriptional regulatory elements for constructing plasmid vectors," *Gene*, 272:149-156 (2001).

Yano et al., "*Ras* oncogene enhances the production of a recombinant protein regulated by the cytomegalovirus promoter in BHK-21 cells," *Cytotechnology*, 16:167-178 (1994).

Zufferey et al., "Woodchuck Hepatitis Virus Posttranscriptional Regulatory Element Enhances Expression of Transgenes Delivered by Retroviral Vectors," *J. Virol.*, 73:2886-2892 (1999).

Breitbart et al., "Gene-enhanced tissue engineering: applications for wound healing using cultured dermal fibroblasts transduced retrovirally with the PDGF-B gene," *Ann. Plast. Surg.*, 1999, 43(6):632-639.

Beddington et al., "An in situ transgenic enzyme marker for the midgestation mouse embryo and the visualization of inner cell mass clones during early organogenesis", Development 106:37-46, 1989.

Garg et al., "The hybrid cytomegalovirus enhancer/chicken β-actin promoter along with woodchuck hepatitis virus posttranscriptional regulatory element enhances the protective efficacy of DNA vaccines", The Journal of Immunology 173:550-558, 2004.

Kim et al., "Gene transfer in bovine blastocysts using replication-defective retroviral vectors packaged with gibbon ape leukemia virus envelopes", Molecular Reproduction and Development 35:105-113, 1993.

Klein et al., "Dose and promoter effects of adeno-associated viral vector for green fluorescent protein expression in the rat brain", Experimental Neurology 176:66-74, 2002.

Klein et al., "Measurements of vector-derived neurotrophic factor and green fluorescent protein levels in the brain", Methods 28:286-292, 2002.

Sawicki et al., "A Composite CMV-IE Enhancer/β-Actin Promoter Is Ubiquitously Expressed in Mouse Cutaneous Epithelium," Exp. Cell Res., 244:367-369 (1998).

GenBank Accession No. NT_039317, dated Feb. 24, 2003, 2 pages.
GenBank Accession No. NW_042778, dated Jan. 29, 2003, 1 page.

* cited by examiner pmAct-Luc-neo pmAct-WPRE-Luc-neo phCMV mAct-Luc-neo pCEF-Luc-neo

SEQUENCE LISTING

```
<160> NUMBER OF SEQ ID NOS: 39

<210> SEQ ID NO 1
<211> LENGTH: 1577
<212> TYPE: DNA
<213> ORGANISM: Mus musculus

<400> SEQUENCE: 1
gggagtgact ctctgtccat tcaatccagg ccccgcgtgt ccctcaaaca agaggccaca      60
caaatagggt ccgggcctcg atgctgaccc tcatccactt aagtgctcga tatccacgtg     120
acatccacac ccagagggtc ctggggtggt tgggtgaccc ccagaatgca ggcctagtaa     180
ccgagacatt gaatggggca gtgtccacaa gggcggaggc tattcctgta catctgggcc     240
tacggagcca gcacccatcg ccaaaactct tcatcctctt cctcaatctc gctttctctc     300 tcgcttttt ttttttttct tcttcttttt tttttttttt ttcaaaagga ggggagaggg     360
ggtaaaaaaa tgctgcactg tgcggcgagg ccggtgagtg agcgacgcgg agccaatcag     420
cgcccgccgt tccgaaagtt gccttttatg gctcgagtgg ccgctgtggc gtcctataaa     480
acccggcggc gcaacgcgca gccactgtcg agtcgcgtcc acccgcgagc acagcttctt     540
tgcagctcct tcgttgccgg tccacacccg ccaccaggta agcagggacg ccgggcccag     600
cgggccttcg ctctctcgtg gctagtacct cactgcaggg tcctgaggat cactcagaac     660
ggacaccatg ggcgggtgga gggtggtgcc gggccgcgga gcggacactg gcacagccaa     720
ctttacgcct agcgtgtaga ctctttgcag ccacattccc gcggtgtaga cactcgtggg     780
cccgctcccg ctcggtgcgt ggggcttggg gacacactag ggtcgcggtg tgggcatttg     840
atgagccggt gcggcttgcg ggtgttaaaa gccgtattag gtccatcttg agagtacaca     900
gtattgggaa ccagacgcta cgatcacgcc tcaatggcct ctgggtcttt gtccaaaccg     960 gttgcctat tcggcttgcc gggcgggcgg gcgggcgggc gggcgcggca gggccggctc    1020
ggccgggtgg gggctgggat gccactgcgc gtgcgctctc tatcactggg catcgaggcg    1080
```

-continued

```
cgtgtgcgct agggagggag ctcttcctct cccctcttc ctagttagct gcgcgtgcgt      1140
attgaggctg ggagcgcggc tgcccggggt tgggcgaggg cggggccgtt gtccggaagg      1200
ggcggggtca cagtggcacg ggcgccttgt ttgcgcttcc tgctgggtgt ggtcgcctcc      1260
cgcgcgcgca caagccgccc gtcggcgcag tgtaggcgga gcttgcgccc gtttggggag      1320
ggggcggagg tctggcttcc tgccctaggt ccgcctccgg gccagcgttt gccttttatg      1380
gtaataatgc ggccggtctg cgcttccttt gtccctgag cttgggcgcg cgccccctgg       1440
cggctcgagc ccgcggcttg ccggaagtgg gcagggcggc agcggctgct cttggcggcc      1500
ccgaggtgac tatagccttc ttttgtgtct tgatagttcg ccatggatga cgatatcgct      1560
gcgctggtcg tcgacaa                                                    1577
```

<210> SEQ ID NO 2
<211> LENGTH: 1542
<212> TYPE: DNA
<213> ORGANISM: Mus musculus

<400> SEQUENCE: 2

```
gggagtgact ctctgtccat tcaatccagg ccccgcgtgt ccctcaaaca agaggccaca       60
caaatagggt ccgggcctcg atgctgaccc tcatccactt aagtgctcga tatccacgtg      120
acatccacac ccgagggtc ctgggtggt tgggtgaccc ccagaatgca ggcctagtaa        180
ccgagacatt gaatggggca gtgtccacaa gggcggaggc tattcctgta catctgggcc      240
tacggagcca gcacccatcg ccaaaactct tcatcctctt cctcaatctc gctttctctc      300 tcgcttttt tttttttct tcttctttt tttttttt ttcaaaagga ggggagaggg          360
ggtaaaaaaa tgctgcactg tgcggcgagg ccggtgagtg agcgacgcgg agccaatcag      420
cgcccgccgt tccgaaagtt gccttttatg gctcgagtgg ccgctgtggc gtcctataaa      480
acccggcggc gcaacgcgca gccactgtcg agtcgcgtcc acccgcgagc acagcttctt      540
tgcagctcct tcgttgccgg tccacacccg ccaccaggta agcagggacg ccgggcccag      600
cgggccttcg ctctctcgtg gctagtacct cactgcaggg tcctgaggat cactcagaac      660
ggacaccatg ggcgggtgga gggtggtgcc gggccgcgga gcggacactg gcacagccaa      720 cttttacgcct agcgtgtaga ctcttttgcag ccacattccc gcggtgtaga cactcgtggg     780
cccgctcccg ctcggtgcgt ggggcttggg gacacactag ggtcgcggtg tgggcatttg      840
atgagccggt gcggcttgcg ggtgttaaaa gccgtattag gtccatcttg agagtacaca      900
gtattgggaa ccagacgcta cgatcacgcc tcaatggcct ctgggtcttt gtccaaaccg      960
gtttgcctat tcggcttgcc gggcggggcg gcggcgggc gggcgcggca gggcggctc      1020 ggccgggtgg gggctgggat gccactgcgc gtgcgctctc tatcactggg catcgaggcg     1080
cgtgtgcgct agggagggag ctcttcctct cccctcttc ctagttagct gcgcgtgcgt     1140
attgaggctg ggagcgcggc tgcccggggt tgggcgaggg cggggccgtt gtccggaagg     1200
ggcggggtca cagtggcacg ggcgccttgt ttgcgcttcc tgctgggtgt ggtcgcctcc     1260
cgcgcgcgca caagccgccc gtcggcgcag tgtaggcgga gcttgcgccc gtttggggag     1320
ggggcggagg tctggcttcc tgccctaggt ccgcctccgg gccagcgttt gccttttatg     1380
gtaataatgc ggccggtctg cgcttccttt gtccctgag cttgggcgcg cgccccctgg      1440
cggctcgagc ccgcggcttg ccggaagtgg gcagggcggc agcggctgct cttggcggcc     1500
ccgaggtgac tatagccttc ttttgtgtct tgatagttcg cc                        1542
```

<210> SEQ ID NO 3
<211> LENGTH: 604
<212> TYPE: DNA
<213> ORGANISM: Woodchuck hepatitis virus

<400> SEQUENCE: 3

```
tctagaaatc aacctctgga ttacaaaatt tgtgaaagat tgactggtat tcttaactat    60
gttgctcctt ttacgctatg tggatacgct gctttaatgc ctttgtatca tgctattgct   120
tcccgtatgg ctttcatttt ctcctccttg tataaatcct ggttgctgtc tctttatgag   180
gagttgtggc ccgttgtcag gcaacgtggc gtggtgtgca ctgtgtttgc tgacgcaacc   240
cccactggtt ggggcattgc caccacctgt cagctccttt ccgggacttt cgctttcccc   300
ctccctattg ccacggcgga actcatcgcc gcctgccttg cccgctgctg acaggggct    360
cggctgttgg gcactgacaa ttccgtggtg ttgtcgggga agctgacgtc ctttccatgg   420
ctgctcgcct gtgttgccac ctggattctg cgcgggacgt ccttctgcta cgtcccttcg   480
gccctcaatc cagcggacct tccttcccgc ggcctgctgc cggctctgcg gcctcttccg   540
cgtcttcgcc ttcgccctca gacgagtcgg atctcccttt gggccgcctc cccgcctgtc   600
taga                                                                604
```

<210> SEQ ID NO 4
<211> LENGTH: 366
<212> TYPE: DNA
<213> ORGANISM: Homo sapiens

<400> SEQUENCE: 4

```
tagttattaa tagtaatcaa ttacggggtc attagttcat agcccatata tggagttccg    60
cgttacataa cttacggtaa atggcccgcc tggctgaccg cccaacgacc cccgcccatt   120
gacgtcaata atgacgtatg ttcccatagt aacgccaata gggactttcc attgacgtca   180
atgggtggag tatttacggt aaactgccca cttggcagta catcaagtgt atcatatgcc   240
aagtacgccc cctattgacg tcaatgacgg taaatggccc gcctggcatt atgcccagta   300
catgacctta tgggactttc ctacttggca gtacatctac gtattagtca tcgctattac   360
catggt                                                              366
```

<210> SEQ ID NO 5
<211> LENGTH: 660
<212> TYPE: DNA
<213> ORGANISM: Mus musculus

<400> SEQUENCE: 5

```
tcctggattg gcagccgctg tagaagctat gacagaatac aagcttgtgg tggtgggcgc    60
tggaggcgtg ggaaagagtg ccctgaccat ccagctgatc cagaaccact tgtggacga   120
gtatgatccc actatagagg actcctaccg gaaacaggtg gtcattgatg gggagacatg   180
tctactggac atcttagaca cagcaggtca agaagagtat agtgccatgc gggaccagta   240
catgcgcaca ggggagggct tcctctgtgt atttgccatc aacaacacca gtcccttcga   300
ggacatccat cagtacaggg agcagatcaa gcgggtgaaa gattcagatg atgtgccaat   360
ggtgctggtg gcaacaagt gtgacctggc tgctcgcact gttgagtctc ggcaggccca   420
ggaccttgct cgcagctatg gcatccccta cattgaaaca tcagccaaga cccggcaggg   480
cgtggaggat gccttctata cactagtccg tgagattcgg cagcataaat gcggaaact   540
gaacccaccc gatgagagtg gtcctggctg catgagctgc aaatgtgtgc tgtcctgaca   600
ccaggtgagg caggaccag cgagacgtct ggggcagtga cctcagctag ccagatgaac   660
```

<210> SEQ ID NO 6
<211> LENGTH: 576
<212> TYPE: DNA
<213> ORGANISM: Mus musculus

<400> SEQUENCE: 6

```
gccaccatga cagaatacaa gcttgtggtg gtgggcgctg gaggcgtggg aaagagtgcc      60
ctgaccatcc agctgatcca gaaccacttt gtggacgagt atgatcccac tatagaggac     120
tcctaccgga acaggtggt cattgatggg gagacatgtc tactggacat cttagacaca      180
gcaggtcaag aagagtatag tgccatgcgg gaccagtaca tgcgcacagg ggagggcttc     240
ctctgtgtat ttgccatcaa caacaccaag tccttcgagg acatccatca gtacagggag     300
cagatcaagc gggtgaaaga ttcagatgat gtgccaatgg tgctggtggg caacaagtgt     360
gacctggctg ctcgcactgt tgagtctcgg caggcccagg accttgctcg cagctatggc     420
atcccctaca ttgaaacatc agccaagacc cggcagggcg tggaggatgc cttctataca     480
ctagtccgtg agattcggca gcataaattg cggaaactga acccacccga tgagagtggt     540
cctggctgca tgagctgcaa atgtgtgctg tcctga                              576
```

<210> SEQ ID NO 7
<211> LENGTH: 189
<212> TYPE: PRT
<213> ORGANISM: Mus musculus

<400> SEQUENCE: 7

```
Met Thr Glu Tyr Lys Leu Val Val Val Gly Ala Val Gly Val Gly Lys
1               5                   10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
        50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His Gln Tyr
                85                  90                  95

Arg Glu Gln Ile Lys Arg Val Lys Asp Ser Asp Asp Val Pro Met Val
            100                 105                 110

Leu Val Gly Asn Lys Cys Asp Leu Ala Ala Arg Thr Val Glu Ser Arg
        115                 120                 125

Gln Ala Gln Asp Leu Ala Arg Ser Tyr Gly Ile Pro Tyr Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln His Lys Leu Arg Lys Leu Asn Pro Pro Asp Glu
                165                 170                 175

Ser Gly Pro Gly Cys Met Ser Cys Lys Cys Val Leu Ser
            180                 185
```

<210> SEQ ID NO 8
<211> LENGTH: 188
<212> TYPE: PRT
<213> ORGANISM: Homo sapiens

<400> SEQUENCE: 8

```
Met Thr Glu Tyr Lys Leu Val Val Gly Ala Val Gly Val Gly Lys
1               5                  10                 15

Ser Ala Leu Thr Ile Gln Leu Ile Gln Asn His Phe Val Asp Glu Tyr
            20                  25                 30

Asp Pro Thr Ile Glu Asp Ser Tyr Arg Lys Gln Val Val Ile Asp Gly
            35                  40                 45

Glu Thr Cys Leu Leu Asp Ile Leu Asp Thr Ala Gly Gln Glu Glu Tyr
    50                  55                 60

Ser Ala Met Arg Asp Gln Tyr Met Arg Thr Gly Glu Gly Phe Leu Cys
65              70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
                100                 105                110

Leu Val Gly Asn Lys Cys Asp Leu Pro Ser Arg Thr Val Asp Thr Lys
                115                 120                125

Gln Ala Gln Asp Leu Ala Arg Ser Tyr Gly Ile Pro Phe Ile Glu Thr
            130                 135                 140

Ser Ala Lys Thr Arg Gln Gly Val Asp Asp Ala Phe Tyr Thr Leu Val
145             150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
                180                 185
```

<210> SEQ ID NO 9
<211> LENGTH: 27
<212> TYPE: DNA
<213> ORGANISM: Artificial
<220> FEATURE:
<223> OTHER INFORMATION: Description of Artificial Sequence :
    Artificially Synthesized Primer Sequence

<400> SEQUENCE: 9
gggagtgact ctctgtccat tcaatcc                                27

<210> SEQ ID NO 10
<211> LENGTH: 27
<212> TYPE: DNA
<213> ORGANISM: Artificial
<220> FEATURE:
<223> OTHER INFORMATION: Description of Artificial Sequence :
    Artificially Synthesized Primer Sequence

<400> SEQUENCE: 10
ttgtcgacga ccagcgcagc gatatcg                                27

<210> SEQ ID NO 11
<211> LENGTH: 26
<212> TYPE: DNA
<213> ORGANISM: Artificial
<220> FEATURE:
<223> OTHER INFORMATION: Description of Artificial Sequence :
    Artificially Synthesized Primer Sequence

<400> SEQUENCE: 11
agatctggga gtgactctct gtccat                                 26

<210> SEQ ID NO 12
<211> LENGTH: 26
<212> TYPE: DNA

<213> ORGANISM: Artificial
<220> FEATURE:
<223> OTHER INFORMATION: Description of Artificial Sequence :
      Artificially Synthesized Primer Sequence

<400> SEQUENCE: 12
aagcttggcg aactatcaag acacaa                                            26

<210> SEQ ID NO 13
<211> LENGTH: 50
<212> TYPE: DNA
<213> ORGANISM: Artificial
<220> FEATURE:
<223> OTHER INFORMATION: Description of Artificial Sequence :
      Artificially Synthesized Primer Sequence

<400> SEQUENCE: 13
aatcaacctc tggattacaa aatttgtgaa agattgactg gtattcttaa                  50

<210> SEQ ID NO 14
<211> LENGTH: 50
<212> TYPE: DNA
<213> ORGANISM: Artificial
<220> FEATURE:
<223> OTHER INFORMATION: Description of Artificial Sequence :
      Artificially Synthesized Primer Sequence

<400> SEQUENCE: 14
gcgtatccac atagcgtaaa aggagcaaca tagttaagaa taccagtcaa                  50

<210> SEQ ID NO 15
<211> LENGTH: 50
<212> TYPE: DNA
<213> ORGANISM: Artificial
<220> FEATURE:
<223> OTHER INFORMATION: Description of Artificial Sequence :
      Artificially Synthesized Primer Sequence

<400> SEQUENCE: 15
acgctatgtg gatacgctgc tttaatgcct ttgtatcatg ctattgcttc                  50

<210> SEQ ID NO 16
<211> LENGTH: 50
<212> TYPE: DNA
<213> ORGANISM: Artificial
<220> FEATURE:
<223> OTHER INFORMATION: Description of Artificial Sequence :
      Artificially Synthesized Primer Sequence

<400> SEQUENCE: 16
ttatacaagg aggagaaaat gaaagccata cgggaagcaa tagcatgata                  50

<210> SEQ ID NO 17
<211> LENGTH: 50
<212> TYPE: DNA
<213> ORGANISM: Artificial
<220> FEATURE:
<223> OTHER INFORMATION: Description of Artificial Sequence :
      Artificially Synthesized Primer Sequence

<400> SEQUENCE: 17
ttctcctcct tgtataaatc ctggttgctg tctctttatg aggagttgtg                  50

<210> SEQ ID NO 18
<211> LENGTH: 50
<212> TYPE: DNA
<213> ORGANISM: Artificial
<220> FEATURE:

<223> OTHER INFORMATION: Description of Artificial Sequence :
      Artificially Synthesized Primer Sequence

<400> SEQUENCE: 18
gtgcacacca cgccacgttg cctgacaacg ggccacaact cctcataaag        50

<210> SEQ ID NO 19
<211> LENGTH: 50
<212> TYPE: DNA
<213> ORGANISM: Artificial
<220> FEATURE:
<223> OTHER INFORMATION: Description of Artificial Sequence :
      Artificially Synthesized Primer Sequence

<400> SEQUENCE: 19
cgtggcgtgg tgtgcactgt gtttgctgac gcaaccccca ctggttgggg        50

<210> SEQ ID NO 20
<211> LENGTH: 50
<212> TYPE: DNA
<213> ORGANISM: Artificial
<220> FEATURE:
<223> OTHER INFORMATION: Description of Artificial Sequence :
      Artificially Synthesized Primer Sequence

<400> SEQUENCE: 20
gtcccggaaa ggagctgaca ggtggtggca atgccccaac cagtgggggt        50

<210> SEQ ID NO 21
<211> LENGTH: 50
<212> TYPE: DNA
<213> ORGANISM: Artificial
<220> FEATURE:
<223> OTHER INFORMATION: Description of Artificial Sequence :
      Artificially Synthesized Primer Sequence

<400> SEQUENCE: 21
cagctccttt ccgggacttt cgctttcccc ctccctattg ccacggcgga        50

<210> SEQ ID NO 22
<211> LENGTH: 50
<212> TYPE: DNA
<213> ORGANISM: Artificial
<220> FEATURE:
<223> OTHER INFORMATION: Description of Artificial Sequence :
      Artificially Synthesized Primer Sequence

<400> SEQUENCE: 22
tgtccagcag cgggcaaggc aggcggcgat gagttccgcc gtggcaatag        50

<210> SEQ ID NO 23
<211> LENGTH: 50
<212> TYPE: DNA
<213> ORGANISM: Artificial
<220> FEATURE:
<223> OTHER INFORMATION: Description of Artificial Sequence :
      Artificially Synthesized Primer Sequence

<400> SEQUENCE: 23
ttgcccgctg ctggacaggg gctcggctgt tgggcactga caattccgtg        50

<210> SEQ ID NO 24
<211> LENGTH: 50
<212> TYPE: DNA
<213> ORGANISM: Artificial
<220> FEATURE:
<223> OTHER INFORMATION: Description of Artificial Sequence :
      Artificially Synthesized Primer Sequence

```
<400> SEQUENCE: 24
ccatggaaag gacgtcagct tccccgacaa caccacggaa ttgtcagtgc                50

<210> SEQ ID NO 25
<211> LENGTH: 50
<212> TYPE: DNA
<213> ORGANISM: Artificial
<220> FEATURE:
<223> OTHER INFORMATION: Description of Artificial Sequence :
      Artificially Synthesized Primer Sequence

<400> SEQUENCE: 25
tgacgtcctt tccatggctg ctcgcctgtg ttgccacctg gattctgcgc                50

<210> SEQ ID NO 26
<211> LENGTH: 50
<212> TYPE: DNA
<213> ORGANISM: Artificial
<220> FEATURE:
<223> OTHER INFORMATION: Description of Artificial Sequence :
      Artificially Synthesized Primer Sequence

<400> SEQUENCE: 26
gagggccgaa gggacgtagc agaaggacgt cccgcgcaga atccaggtgg                50

<210> SEQ ID NO 27
<211> LENGTH: 50
<212> TYPE: DNA
<213> ORGANISM: Artificial
<220> FEATURE:
<223> OTHER INFORMATION: Description of Artificial Sequence :
      Artificially Synthesized Primer Sequence

<400> SEQUENCE: 27
acgtcccttc ggccctcaat ccagcggacc ttccttcccg cggcctgctg                50

<210> SEQ ID NO 28
<211> LENGTH: 57
<212> TYPE: DNA
<213> ORGANISM: Artificial
<220> FEATURE:
<223> OTHER INFORMATION: Description of Artificial Sequence :
      Artificially Synthesized Primer Sequence

<400> SEQUENCE: 28
gagggcgaag gcgaagacgc ggaagaggcc gcagagccgg cagcaggccg cgggaag       57

<210> SEQ ID NO 29
<211> LENGTH: 56
<212> TYPE: DNA
<213> ORGANISM: Artificial
<220> FEATURE:
<223> OTHER INFORMATION: Description of Artificial Sequence :
      Artificially Synthesized Primer Sequence

<400> SEQUENCE: 29
gtcttcgcct tcgccctcag acgagtcgga tctcccttg ggccgcctcc ccgcct          56

<210> SEQ ID NO 30
<211> LENGTH: 30
<212> TYPE: DNA
<213> ORGANISM: Artificial
<220> FEATURE:
<223> OTHER INFORMATION: Description of Artificial Sequence :
      Artificially Synthesized Primer Sequence

<400> SEQUENCE: 30
```

```
tctagaaatc aacctctgga ttacaaaatt                                    30
```

```
<210> SEQ ID NO 31
<211> LENGTH: 26
<212> TYPE: DNA
<213> ORGANISM: Artificial
<220> FEATURE:
<223> OTHER INFORMATION: Description of Artificial Sequence :
      Artificially Synthesized Primer Sequence

<400> SEQUENCE: 31
tctagaaggc ggggaggcgg cccaaa                                        26
```

```
<210> SEQ ID NO 32
<211> LENGTH: 25
<212> TYPE: DNA
<213> ORGANISM: Artificial
<220> FEATURE:
<223> OTHER INFORMATION: Description of Artificial Sequence :
      Artificially Synthesized Primer Sequence

<400> SEQUENCE: 32
atcctggttg ctgtctcttt atgag                                         25
```

```
<210> SEQ ID NO 33
<211> LENGTH: 22
<212> TYPE: DNA
<213> ORGANISM: Artificial
<220> FEATURE:
<223> OTHER INFORMATION: Description of Artificial Sequence :
      Artificially Synthesized Primer Sequence

<400> SEQUENCE: 33
gtgcacacca cgccacgttg cc                                            22
```

```
<210> SEQ ID NO 34
<211> LENGTH: 27
<212> TYPE: DNA
<213> ORGANISM: Artificial
<220> FEATURE:
<223> OTHER INFORMATION: Description of Artificial Sequence :
      Artificially Synthesized Primer Sequence

<400> SEQUENCE: 34
tcctggattg gcagccgctg tagaagc                                       27
```

```
<210> SEQ ID NO 35
<211> LENGTH: 27
<212> TYPE: DNA
<213> ORGANISM: Artificial
<220> FEATURE:
<223> OTHER INFORMATION: Description of Artificial Sequence :
      Artificially Synthesized Primer Sequence

<400> SEQUENCE: 35
gttcatctgg ctagctgagg tcactgc                                       27
```

```
<210> SEQ ID NO 36
<211> LENGTH: 24
<212> TYPE: DNA
<213> ORGANISM: Artificial
<220> FEATURE:
<223> OTHER INFORMATION: Description of Artificial Sequence :
      Artificially Synthesized Primer Sequence

<400> SEQUENCE: 36
gccaccatga cagaatacaa gctt                                          24
```

```
<210> SEQ ID NO 37
<211> LENGTH: 20
<212> TYPE: DNA
<213> ORGANISM: Artificial
<220> FEATURE:
<223> OTHER INFORMATION: Description of Artificial Sequence :
      Artificially Synthesized Primer Sequence

<400> SEQUENCE: 37
tcaggacagc acacatttgc                                           20

<210> SEQ ID NO 38
<211> LENGTH: 27
<212> TYPE: DNA
<213> ORGANISM: Artificial
<220> FEATURE:
<223> OTHER INFORMATION: Description of Artificial Sequence :
      Artificially Synthesized Primer Sequence

<400> SEQUENCE: 38
gtggtgggcg ctgtaggcgt gggaaag                                   27

<210> SEQ ID NO 39
<211> LENGTH: 27
<212> TYPE: DNA
<213> ORGANISM: Artificial
<220> FEATURE:
<223> OTHER INFORMATION: Description of Artificial Sequence :
      Artificially Synthesized Primer Sequence

<400> SEQUENCE: 39
ctttcccacg cctacagcgc ccaccac                                   27
```

EXPRESSION SYSTEMS USING MAMMALIAN BETA-ACTIN PROMOTER

CROSS-REFERENCE TO RELATED APPLICATIONS

This application is the National Stage of International Application No. PCT/JP2004/018006, filed on Dec. 3, 2004, which claims the benefit of Japanese Patent Application Serial No. 2003-405269, filed on Dec. 3, 2003. The contents of both of the foregoing applications are hereby incorporated by reference in their entireties.

TECHNICAL FIELD

The present invention relates to the development of stronger promoters for the production of recombinant proteins, and vectors carrying the promoters.

BACKGROUND ART

In recent years, many biopharmaceuticals have been released into the market. Most of such pharmaceuticals are products of recombinant proteins obtained by introducing genes into animal cells. Technologies for efficient production of such recombinant proteins in animal cells enable biopharmaceutical cost reduction and promise a stable supply to patients.

Conventionally, elongation factor 1 (EF1) α promoter, SRα promoter, and the like were used in such expression vectors (Patent Document 1; Non-Patent Documents 1 and 2). Recently, as a result of further improvements for efficient expression, strong promoters such as the human CMV enhancer combined with chicken β-actin promoter (CAG promoter) and human CMV enhancer combined with human EF1α promoter (CEF promoter) have been constructed and used for the purpose described above (Non-Patent Documents 3 to 5).

However, the need to develop vectors having stronger promoters is still remained. Such vectors are expected to contribute greatly to a further reduction of costs and a more stable supply of biopharmaceuticals.

Patent Document 1: WO92/19759
Non-Patent Document 1: Mol. Cell. Biol., Vol. 8 (1), p. 466-472, 1988
Non-Patent Document 2: Gene, Vol. 87(2), p. 291-294, 1990
Non-Patent Document 3: Gene, Vol. 272, p. 149-156, 2001
Non-Patent Document 4: Analytical Biochemistry, Vol. 247, p. 179-181, 1997
Non-Patent Document 5: Gene, Vol. 108, p. 193-200, 1991

DISCLOSURE OF THE INVENTION

Problems to be Solved by the Invention

The present invention was conducted under the above circumstances. An objective of the present invention is to provide promoters stronger than existing animal cell expression promoters, and vectors using such promoters. Another objective of the present invention is to develop methods for producing desired proteins using the vectors, and methods for expressing desired DNAs using the vectors.

Means to Solve the Problems

The present inventors tested and compared promoter activities using combinations of promoters and enhancers from various genes to achieve the objectives described above.

First, the 5' region of mouse β-actin was amplified by PCR, based on information on the mouse β-actin sequence obtained from mouse genome information disclosed at NCBI and the Jackson laboratory. The amplified PCR product was cloned into pGEM-T-Easy vector, and the nucleotide sequence was confirmed by sequencing. Then, only the promoter region of mouse β-actin was amplified by PCR, and inserted into BglII-HindIII site of pGL3-Basic. A neomycin-resistant gene was then inserted into the vector to give pmAct-Luc-neo.

The post-transcriptional regulatory region in the genomic sequence of Woodchuck hepatitis virus (WPRE) was then amplified by PCR. The reaction product was cloned into pGEM-T-Easy vector, and the nucleotide sequence was determined. Then, this pGEM-T/WPRE was digested with XbaI, and the resulting WPRE fragment was inserted into the XbaI site of pmAct-Luc-neo to give pmAct-WPRE-Luc-neo.

Then, the expression vector pmAct-Luc-neo was constructed by inserting a CMV enhancer region into the multicloning site (MCS; 5th to 53rd nucleotide) of pGL3-Basic vector; and the expression vector phCMV-mAct-Luc-neo was constructed by inserting human CMV enhancer-mouse β-actin promoter into the MCS (FIG. 1).

As a control vector, pCEF-Luc-neo was constructed by inserting human EF1α promoter derived from DHFR-ΔE-RVh-PM1-f (see, WO 92/19759), and CMV enhancer, into MCS of pGLN vector (FIG. 1).

These vectors were independently introduced into CHO cells. The cells were cultured in a $CO_2$ incubator for two days and assayed for luciferase activity using the Luciferase Assay System. The results showed that the constructed pmAct-Luc-neo had significantly higher activity than the other vectors (FIG. 2). Thus, the mouse β-actin promoter of the present invention was found to be stronger than the existing CEF promoter. In addition, it was also found that the activity of the mouse β-actin promoter can be significantly enhanced by attaching the WPRE element or CMV enhancer thereto (FIG. 3).

The present inventors then tested the effect of transactivator coexpression. pCXN-H-Ras (mouse c-H-ras), pCXN-A-H-Ras (activated mouse c-H-ras), and pCXN-A-K-Ras (activated human K-ras) were constructed by cloning mouse c-H-ras gene, activated mouse c-H-ras, and activated human K-ras; and inserting them into pCXN vector, respectively. Two or three types of the vectors were co-introduced at various ratios into CHO cells, and the luciferase activities were determined. The results showed that the promoter activity of pmAct-Luc-neo was enhanced in the presence of pCXN-H-Ras (mouse c-H-ras), pCXN-A-H-Ras (activated mouse c-H-ras), or pCXN-A-K-Ras (activated human c-K-ras) (FIG. 4). These findings showed that the oncogene product Ras (regardless of whether it is in the active form, wild type, H-Ras, or K-Ras) confers stronger activity to the mouse β-actin promoter of the present invention.

Specifically, the present inventors found that the combination of CMV enhancer and mammalian β-actin promoter, and the combination of the post-transcriptional regulatory region of Woodchuck Hepatitis Virus genomic sequence (WPRE) and mammalian β-actin promoter could serve as strong promoters. The present inventors also found that in expression systems carrying these promoters, the expression activity can be further enhanced by co-expressing the oncogene product Ras, which is a transactivator, thus completing the present invention.

More specifically, the present invention relates to the following [1]-[37].

[1] A DNA construct, wherein a mammalian β-actin promoter is operably linked to an enhancer.

[2] The DNA construct of [1], wherein the enhancer is derived from Cytomegalovirus (CMV).

[3] The DNA construct of [1], wherein the enhancer is Woodchuck Hepatitis Virus Posttranscriptional Regulatory Element (WPRE).

[4] The DNA construct of any one of [1] to [3], wherein the mammalian β-actin promoter is a rodent β-actin promoter.

[5] The DNA construct of [2], wherein the CMV enhancer comprises the nucleotide sequence shown in SEQ ID NO: 4 and the mammalian β-actin promoter comprises the nucleotide sequence shown in SEQ ID NO: 2.

[6] The DNA construct of [3], wherein the Woodchuck Hepatitis Virus Posttranscriptional Regulatory Element (WPRE) comprises the nucleotide sequence shown in SEQ ID NO: 3 and the mammalian β-actin promoter comprises the nucleotide sequence shown in SEQ ID NO: 2.

[7] A vector comprising the DNA construct of any one of [1] to [6].

[8] The vector of [7], comprising a DNA having a desired DNA operably linked downstream of the mammalian β-actin promoter.

[9] The vector of [7] or [8], comprising and capable of expressing a DNA encoding a transactivator.

[10] The vector of [9], wherein the transactivator is an oncogene product.

[11] The vector of [10], wherein the oncogene product is Ras.

[12] The vector of any one of [8] to [11], wherein the desired DNA encodes a desired protein.

[13] A cell comprising the vector of any one of [8] to [12].

[14] A cell comprising the vector of any one of [8] to [12], wherein the oncogene is activated.

[15] The cell of [14], into which the vector comprising the gene encoding the transactivator is introduced.

[16] The cell of [14], which is a transformed cell.

[17] The cell of any one of [13] to [16], which is a mammalian cell.

[18] The cell of [17], which is a rodent cell.

[19] The cell of any one of [13] to [18], which is derived from the same animal order as that from which the β-actin promoter is derived.

[20] The cell of [19], which is derived from the same animal species as that from which the β-actin promoter is derived.

[21] A non-human transgenic animal into which the vector according to any one of [8] to [12] has been introduced.

[22] A totipotent cell into which the vector of any one of [8] to [12] is introduced.

[23] A method for producing a desired protein, which comprises culturing a cell comprising the vector of [12]; and harvesting the expressed protein from the cultured cell or medium.

[24] The method of [23], which comprises adding a transactivator to the medium.

[25] A method for expressing a desired DNA in a host cell, which comprises introducing the vector of any one of [8] to [12] into the host cell derived from the same animal order as that from which the β-actin promoter in the vector is derived.

[26] A method for expressing a desired DNA in a host cell, which comprises introducing the vector of any one of [8] to [12] into a host cell derived from the same animal species as that from which the β-actin promoter in the vector is derived.

[27] A method for expressing a desired DNA in a host cell, which comprises introducing the vector of [8] and a vector comprising and capable of expressing a DNA encoding a transactivator into a host cell which is derived from the same species as that from which the β-actin promoter in the vector of [8] is derived.

[28] The method of any one of [25] to [27], wherein the host cell is a mammalian cell.

[29] The method of any one of [25] to [27], wherein the host cell is a rodent cell.

[30] A method for increasing the expression level of a desired DNA in the host cell, which comprises inserting upstream of the desired DNA a β-actin promoter derived from the same animal order as that from which the host cell is derived.

[31] A method for increasing the expression level of a desired DNA in the host cell, which comprises inserting upstream of the desired DNA a β-actin promoter derived from the same animal species as that from which the host cell is derived.

[32] The method of [30] or [31], which further comprises inserting an enhancer.

[33] The method of [32], wherein the enhancer is Woodchuck Hepatitis Virus Posttranscriptional Regulatory Element (WPRE).

[34] The method of [32], wherein the enhancer is a CMV enhancer.

[35] The method of any one of [30] to [34], which comprises inserting a gene encoding a transactivator gene.

[36] The method of any one of [30] to [35], wherein the host cell is a mammalian cell.

[37] The method of any one of [30] to [35], wherein the host cell is a rodent cell.

DETAILED DESCRIPTION

Figure 1:
FIG. 1 is a diagram showing the vectors used in the experiments.
Figure 1:
Figure 1:
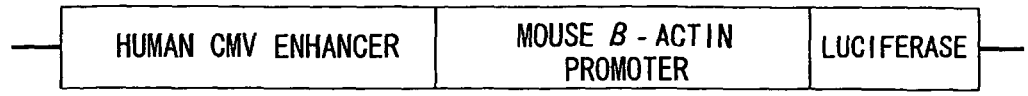
Figure 1:
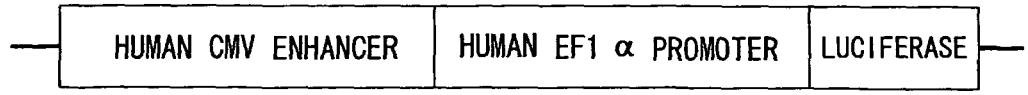

The present invention provides DNA constructs in which a mammalian β-actin promoter is operably linked to an enhancer, and vectors carrying the DNA constructs. The DNA constructs and vectors of the present invention can be used for the expression of desired DNAs (for example, the expression of DNAs encoding a desired protein, antisense DNAs, and DNAs encoding dsRNAs).

Herein, mammalian β-actin promoter is "operably linked" to an enhancer means that the enhancer and the mammalian β-actin promoter having the promoter activity of the present invention are linked together such that the promoter activity is enhanced. Therefore, the phrase "operably linked" also includes cases where the mammalian β-actin promoter is apart from the enhancer or where a certain gene is inserted between them, as long as the promoter activity of the mammalian β-actin promoter is enhanced. The enhancer may be located upstream or downstream of the mammalian β-actin promoter.

The mammalian β-actin promoter and a desired DNA are "operably linked" means that the mammalian β-actin promoter and the desired DNA are linked together such that the expression of the desired DNA is induced through the activation of the mammalian β-actin promoter. Any DNA sequence may exist between the DNA and the mammalian β-actin promoter, as long as the expression of the DNA can be induced. Herein, "expression of DNA" includes both transcription and translation. The desired DNA may encode a desired protein.

In the present invention, there is no limitation on the type of the enhancers, as long as they consequently increase the amount of messenger RNAs (mRNAs) produced through transcription. Enhancers are nucleotide sequences that have the effect of enhancing promoter activity, and in general, often comprise about 100 bp. Enhancers can enhance transcription regardless of the orientation of their sequence. While enhancers themselves have no promoter activity, they can activate transcription from a distance of several kilo base pairs. Furthermore, enhancers may be located upstream or downstream of a gene region to be transcribed, and also may be located within the gene, to activate the transcription. As described above, there is no limitation on the type of the enhancers of the present invention, as long as they increase the amount of mRNAs produced through transcription. Therefore, the enhancers of the present invention also include those that increase the amount of mRNAs in cells and enhance the efficiency of amino acid translation through inhibition of mRNA degradation or stabilization of mRNAs after mRNA transcription.

A single enhancer, or two or more of identical enhancers, may be used as the enhancers of the present invention. Different types of enhancers may be also used in combination.

The enhancers used in the present invention include: WPRE; CMV enhancers; the R-U5' segment in LTR of HTLV-I (Mol. Cell. Biol., Vol. 8(1), p. 466-472, 1988); SV40 enhancer; the intron sequence between exons 2 and 3 of rabbit β-globin (Proc. Natl. Acad. Sci. USA., Vol. 78(3), p. 1527-31, 1981); and the genome region of human growth hormone (J Immunol., Vol. 155(3), p. 1286-95, 1995). Preferred enhancers are WPRE and CMV enhancers.

WPRE has been reported to be a region similar to the human hepatitis B virus posttranscriptional regulatory element (HBVPRE) present in the Woodchuck hepatitis virus genomic sequence (GenBank Accession No. J04514), and that the 592 nucleotides from position 1093 to 1684 of this genomic sequence correspond to the post-transcriptional regulatory region (Journal of Virology, Vol. 72, p. 5085-5092, 1998). Later, analyses using retroviral vectors revealed that WPRE inserted into the 3'-terminal untranslated region of a gene of interest increases the amount of protein produced by 5 to 8 folds. It has also been reported that the introduction of WPRE suppresses mRNA degradation (Journal of Virology, Vol. 73, p. 2886-2892, 1999). In a broad sense, elements such as WPRE that increase the efficiency of amino acid translation by stabilizing mRNAs are also thought to be enhancers. The WPRE used in the present invention is more preferably the DNA comprising the nucleotide sequence shown in SEQ ID NO: 3.

A CMV enhancer can also be used for the same purpose as that for WPRE. Cytomegaloviruses used in the present invention may be those infectious to humans (human Cytomegalovirus) or those infectious to non-human animals. Cytomegaloviruses that are infectious to non-human animals include, for example, those infectious to rodents (e.g., mouse Cytomegalovirus). The CMV enhancers include those of which sequences are known. For example, the CMV enhancers of GenBank Accession No. X17403 (human Cytomegalovirus) and GenBank Accession No. L06816 (mouse Cytomegalovirus) may be used. Many commercially available expression vectors carry CMV enhancers as a part of CMV promoters (for example, pCMV-Script from Stratagene and pcDNA3.1 from Invitrogen). A more preferable CMV enhancer used in the present invention is a DNA comprising the nucleotide sequence shown in SEQ ID NO: 4.

Promoters are specific nucleotide sequences in DNAs that allow initiation of transcription using DNAs as templates, and have a consensus sequence in general. For example, promoters in prokaryotes such as *E. coli* typically include TATAATG and TTGACA sequences located at −10 and −35 bp, respectively, from the transcription initiation site. Eukaryotic promoters typically include a TATA box at −20 bp.

A mammalian β-actin promoter can be used as a β-actin promoter in the present invention. The mammalian β-actin promoter may be derived from any mammal, including human and rodent. A rodent β-actin promoter can be preferably used. As a rodent β-actin promoter, for example, mouse β-actin promoter (GenBank Accession No. NT_039317) and rat β-actin promoter (GenBank Accession No. NW_042778) can be used. The DNA comprising the nucleotide sequence shown in SEQ ID NO: 1 or 2 is more preferred as a mammalian β-actin promoter used in the present invention.

Rodents include animals belonging to, for example, Myomodonta, Sciuromorpha, Castorimorpha, Protrogomorpha, Bathygeromorphi, Hystricognatha, and Caviomorpha, and more specifically include mice, rats, and hamsters.

"Vectors" generally refer to carrier DNA molecules for introducing a desired gene into hosts, and amplifying and expressing the desired gene. Preferably, vectors have auxotrophic genes, and have known restriction sites and the ability to replicate in hosts. In general, vectors may comprise a promoter, an enhancer, a terminator, SD sequence, translation initiation and termination codons, and a replication origin. If required, vectors may further comprise selection markers for selecting cells to which the vectors have been introduced. Such selection markers include: genes resistant to drugs such as ampicillin, tetracycline, kanamycin, chloramphenicol, neomycin, hygromycin, puromycin, and zeocin; markers that allow the selection using as an indicator an activity of an enzyme such as galactosidase; and markers such as GFP that allow selection using fluorescence emission as an indicator. It is also possible to use selection markers that allow selection using as an indicator a surface antigen such as EGF receptor and B7-2. By using such selection markers, only cells into which vectors have been introduced, more specifically cells into which the vectors of the present invention have been introduced, can be selected. The vectors may comprise signal sequences for polypeptide secretion. As a signal sequence for polypeptide secretion, pelB signal sequence (J. Bacteriol., Vol. 169(9), p. 4379-4383, 1987) can be used when the polypeptides are produced into periplasm of *E. coli*.

There is no limitation on the type of vectors to be used in the present invention; any vector may be used. Specifically, the vectors include mammalian vectors (for example, pcDNA3 (Invitrogen), pEGF-BOS (Nucleic Acids. Res., 18(17), p. 5322, 1990), pEF, pCDM8, and pCXN, vectors derived from insect cells (for example, "Bac-to-BAC baculovirus expression system" (Invitrogen), pBacPAK8), plant-derived expression vectors (for example, pMH1 and pMH2), animal virus-derived vectors (for example, pHSV, pMV, and pAdexLcw), retrovirus-derived vectors (for example, pZIP-neo), yeast-derived vectors (for example, "*Pichia* Expression Kit" (Invitrogen), pNV11, and SP-Q01), *Bacillus subtilis*-derived vectors (for example, pPL608 and pKTH50), and *E. coli* vectors (M13-type vectors, pUC-type vectors, pBR322, pBluescript, and pCR-Script). In the present invention, it is preferable to use vectors that can be expressed in mammalian cells, and to use expression vectors.

When CHO cells are used as host, to stably express genes and to increase the copy number of genes in cells, it is possible to introduce, into CHO cells lacking the nucleic acid synthesis pathway, a vector comprising DHFR gene (for example, pCHOI) that complements the deficiency, and then amplify the gene using methotrexate (MTX).

The vectors of the present invention may also comprise a DNA encoding a transactivator. The transactivator is a trans-acting factor that activates gene transcription, and is also called transactivation factor. Known transactivators include those which have DNA binding ability and directly enhance transcription through the binding to cis elements, and those which have no DNA binding ability but indirectly enhance transcription by activating other factors. There is no limitation on the type of transactivators used in the present invention, and any transactivator may be used. Specifically, the transactivators include E1A of adenovirus, Tat of human immunodeficiency virus, Tax of human T cell leukemia virus, and oncogene products. Oncogene products are preferably used in the present invention. "Oncogene" is a generic term for a class of genes that originally exist in normal animal cells, but if activated by mutations, induce canceration of cells. Oncogenes in viruses are called viral oncogenes, and the counterpart genes in normal cells from which the oncogenes are derived are called cellular oncogenes. Such oncogenes include, for example, src, yes, fgr, fms, erbB, abl, kit, crk, mos, raf, sis, ras, myc, fos, and jun. It has been reported that activated human H-Ras improves expression efficiency of expression vectors into which the human β-actin promoter is inserted (Cytotechnology, Vol. 16, p. 167-178, 1994). It is also preferable to use Ras in the present invention. Ras includes K-ras, H-ras, N-ras, and c-ras, and when the rho gene family and the rab gene family are included, such genes are called "the ras superfamily". H-ras is preferably used in the present invention. When used as a transactivator, Ras may be in its wild type or active form. H-ras used in the present invention is more preferably the DNA shown in SEQ ID NO: 5 or 6, or a DNA encoding the amino acid sequence of SEQ ID NO: 7 or 8.

Furthermore, the vectors of the present invention may be designed to express the genes in a stage-specific manner. Methods for expressing genes in a stage-specific manner include, for example, methods using site-specific recombination, such as the Cre-loxP system.

Cre is a recombinase derived from *E. coli* bacteriophage P1, which mediates site-specific recombination between two loxP sequences. loxP sequence comprises an 8-bp spacer region located between two flanking 13-bp inverted repeat sequences that serve as recognition sequences for Cre binding. When the loxP sequence is introduced into a vector so as to suppress the expression of a desired gene, the gene can be expressed at desired stages by removing the loxP sequence by Cre administration. The insertion site of the loxP sequence may be any site as long as it can suppress the expression of the desired gene, such as between the promoter and the gene. Cre administration may be achieved by administering Cre itself or a Cre-encoding gene. When the Cre-loxP system is used in animals such as transgenic animals, the desired gene can be expressed, for example, by infecting with an adenovirus that expresses Cre (Nucleic Acids. Res., Vol. 23(19), p. 3816-3821, 1995). Site-specific recombination using such enzymes further include those using Flp-FRT, *Zygosaccharomyces rouxii* pSR1, resolvase-rfsF, phage Mu Gin, and so on.

Methods using antibiotics such as tetracycline, methods using hormones such as ecdysone, and such can be used in addition to the stage-specific expression systems as described above. These methods are known to those skilled in the art, and can be carried out by using commercially available kits (ecdysone expression system (Invitrogen), tetracycline expression system (Clontech), and such).

The present invention also provides host cells into which the vectors of the present invention are introduced. The host cells of the present invention can be used, for example, as a production system to produce and express desired proteins. There is no limitation on the type of host cells into which the vectors of the present invention is to be introduced. Any type of cell including established cell lines, primary cultured cells, animals, and fertilized eggs can serve as the host cell. The host cells of the present invention include, for example, various animal cells (for example, mammalian cells) and *E. coli* cells. For example, animal cells, plant cells, and fungal cells, can be used as the eukaryotic host cells. As animal cells, mammalian cells derived from human, mouse, hamster, and such (for example, CHO, COS, 3T3, myeloma, baby hamster kidney (BHK), HeLa, and Vero), amphibian cells (for example, *Xenopus laevis* oocytes (Nature, Vol. 291, p. 358-360, 1981)), and insect cells (for example, Sf9, Sf21, and Tn5) are known. As CHO cells, in particular, DHFR gene-deficient CHO cells such as dhfr-CHO are preferably used (Proc. Natl. Acad. Sci. USA, Vol. 77, p. 4216-4220, 1980) and CHO K-1 (Proc. Natl. Acad. Sci. USA, Vol. 60, p. 1275, 1968). As plant cells, for example, *Nicotiana tabacum*-derived cells are known as a system for producing polypeptides, and may be cultured as calli. As fungal cells, yeast (for example, *Saccharomyces*, e.g., *Saccharomyces cerevisiae*), and filamentous fungi (for example, *Aspergillus*, e.g., *Aspergillus niger*) are known. Production systems using bacterial cells are available when prokaryotic cells are used. Bacterial cells include *Escherichia coli* (*E. coli*), for example, JM109, DH5α, and HB101, and additionally *Bacillus subtilis*. Host cells of the present invention are preferably animal cells, more preferably mammalian cells, and particularly preferably rodent cells (for example, CHO cell).

Alternatively, cells with an activated oncogene can also be used as the host cells of the present invention. The phrase "cells with an activated oncogene" means cells in which an oncogene is expressed at a higher level as compared to normal cells, or cells in which a mutated oncogene is expressed.

Cells with an activated oncogene may be cells in which the oncogene is activated artificially or non-artificially. Specific examples of cells in which an oncogene is artificially activated include cells into which a vector comprising an oncogene (wild type or active form) has been introduced and cells into which an artificially mutated oncogene has been introduced. Specific examples of cells in which an oncogene is non-artificially activated include cancerated cells (e.g., human bladder cancer cell T24; Nature, Vol. 302, p. 33-37, 1983). The mechanism underlying oncogene activation may include promoter insertion, point mutation, gene amplification, translocation, and so on.

Those skilled in the art can appropriately select methods for introducing the vectors of the present invention into the cells described above, depending on the cell type. For example, the introduction into mammalian cells can be achieved by a method selected from the calcium phosphate method (Virology, Vol. 52, p. 456, 1973), DEAE-dextran method, method using cationic liposome DOTAP (Roche Diagnostics), electroporation (Nucleic Acids Res., Vol. 15, p. 1311, 1987), lipofection (J. Clin. Biochem. Nutr., Vol. 7, p. 175, 1989), introduction methods using viral infection (Sci. Am., p. 34, 1994), particle guns, and such. Introduction into plant cells can be achieved by electroporation (Nature, Vol. 319, p. 791, 1986), polyethylene glycol method (EMBO J., Vol. 3, p. 2717, 1984), particle gun method (Proc. Natl. Acad.

Sci. USA, Vol. 85, p. 8502, 1988), *Agrobacterium*-mediated method (Nucleic Acids Res., Vol. 12, p. 8711, 1984), or such.

Alternatively, kits such as TransIT (TaKaRa), PolyFect Transfection Reagent (QIAGEN), or LipofectAMINE (Invitrogen) may be used. Furthermore, a host cell of the present invention may comprise a vector carrying a DNA encoding a transactivator in addition to the vector of the present invention.

The present invention also relates to methods for producing desired proteins and methods for expressing desired DNAs, using the vectors of the present invention. Production systems for proteins include in-vitro and in-vivo production systems. In-vitro production systems include those using eukaryotic or prokaryotic cells. For example, desired proteins can be obtained by culturing the above-described host cells in vitro. Such a culture can be achieved according to known methods. For example, liquid culture media for animal cells include DMEM, MEM, RPM11640, IMDM, F10 medium, and F12 medium. The culture media may comprise serum supplements such as fetal calf serum (FCS), or may be serum-free culture media. Furthermore, a transactivator may be added to the media. The culture pH is preferably about 6 to 8. The cultivation is typically carried out at about 30° C. to 40° C. for about 15 to 200 hours; if required, the medium is changed, aerated and stirred. Since culture conditionsvary depending on the cell type used, those skilled in the art can appropriately determine suitable conditions. For example, typically, CHO cells may be cultured, under an atmosphere of 0% to 40% $CO_2$ gas, preferably, 2% to 10%, at 30° C. to 39° C., preferably, at about 37° C., for 1 to 14 days. Various culture apparatuses can be used for animal cells, examples being fermentation tank-type tank culture apparatuses, airlift-type culture apparatuses, culture flask-type culture apparatuses, spinner flask-type culture apparatuses, microcarrier-type culture apparatuses, flow tank-type culture apparatuses, hollow fiber-type culture apparatuses, roller bottle-type culture apparatuses, and packed bed-type culture apparatuses.

Meanwhile, in-vivo production systems for proteins include, for example, production systems using animals or plants. A DNA of interest is introduced into such an animal or plant, and the polypeptide produced in the animal or plant in vivo is collected. The "hosts" of the present invention includes such animals and plants. Production systems using animals include systems using mammals or insects. Such mammals include goats, pigs, sheep, mice, and cattle (Vicki Glaser, SPECTRUM Biotechnology Applications, 1993). Transgenic animals can also be used as the mammals. For example, DNAs encoding desired proteins are prepared as fusion genes comprising genes encoding polypeptides such as goat β casein specifically produced into milk. Then, DNA fragments comprising the fusion genes are injected into goat embryos, and the resulting goat embryos are transplanted into female goats. The desired proteins can be obtained from milk produced by transgenic goats born of the goats that have received the embryos, or their progenies. Hormones may be appropriately given to the transgenic goats to increase the amount of milk comprising the polypeptides produced by the transgenic goats (Bio/Technology, Vol. 12, p. 699-702, 1994). In addition, insects such as silkworm can be used. When silkworms are used, they are infected with a baculovirus into which a DNA encoding a desired protein is inserted and the desired protein can be obtained from body fluid (Nature, Vol. 315, p. 592-594, 1985).

Furthermore, when using plants, for example, tobacco may be used. When tobacco is used, a DNA encoding a desired protein is inserted into a plant expression vector, for example, pMON 530, and the vector is introduced into a bacterium such as *Agrobacterium tumefaciens*. Tobacco (for example, *Nicotiana tabacum*) is infected with the bacterium. The desired protein can be obtained from leaves of the resulting tobacco (Eur. J. Immunol., Vol. 24, p. 131-138, 1994).

In the methods of the present invention for producing proteins, the gene expression may be transient. To achieve transient gene expression, for example, methods which comprise transforming COS cells having, on a chromosome, the gene expressing SV40 T antigen with a vector (such as pcD) carrying SV40 replication origin are used. It is also possible to use replication origins derived from polyoma virus, adenovirus, bovine papilloma virus (BPV), and such. Furthermore, to increase the copy number of genes in the host cell line, the expression vectors may comprise aminoglycoside transferase (APH) gene, thymidine kinase (TK) gene, *E. coli* xanthine-guanine phosphoribosyl transferase (Ecogpt) gene, dihydrofolate reductase (dhfr) gene, and such as selection markers. Furthermore, when a desired gene is expressed in vivo, for example, in gene therapy, it is possible to use methods which comprise inserting the desired gene into a vector and introducing the resulting vector into the body, for example, by the retrovirus method, liposome method, cationic liposome method, or adenovirus method. Vectors that can be used include, for example, adenovirus vectors (for example, pAdexlcw) and retroviral vectors (for example, pZIPneo), but are not limited thereto. Ordinary gene manipulations comprising insertion of the desired gene into a vector and such can be preformed according to conventional methods (Molecular Cloning, 5.61-5.63). The introduction to the living body may be carried out ex vivo or in vivo.

Desired proteins obtained by the present invention can be isolated from inside or outside (medium or such) of the host cells and purified as substantially pure homogeneous proteins. The proteins can be isolated and purified by conventional protein isolation/purification methods. There is no limitation on the type of methods for isolating and purifying the proteins. The proteins can be isolated and purified by appropriately selecting and using in combination, a chromatography column, filter, ultrafiltration, salting out, solvent precipitation, solvent extraction, distillation, immunoprecipitation, SDS-polyacrylamide gel electrophoresis, isoelectrofocusing, dialysis, recrystallization, and such. Chromatography includes, for example, affinity chromatography, ion exchange chromatography, hydrophobic chromatography, gel filtration, reverse phase chromatography, and adsorption chromatography (Strategies for Protein Purification and Characterization: A Laboratory Course Manual. Ed Daniel R. Marshak et al., Cold Spring Harbor Laboratory Press, 1996). These chromatographic methods can be conducted using liquid chromatography, for example, HPLC and FPLC. Any modifications or partial removal of peptides can be achieved by reacting the proteins with appropriate protein modification enzymes before or after purification. Such protein modification enzymes include, for example, trypsin, chymotrypsin, lysyl endopeptidase, protein kinase, and glucosidase.

The vectors, DNA constructs, or host cells of the present invention can be used to produce desired proteins. In the present invention, the desired proteins may be any proteins, including protein fragments and peptides. Specifically, the desired proteins include, for example, antibodies, cytokines, and growth factors, such as erythropoietin, colony-stimulating factor (granulocyte, macrophage, and granulocyte macrophage), interleukins 1 to 31, interferons, RANTES, lymphotoxin β, Fas ligand, flt-3 ligand, ligand (RANKL) for NF-κB receptor activation factor, TNF-related apoptosis-inducing ligand (TRAIL), CD40 ligand, OX40 ligand, 4-1BB ligand (and other members belonging to the TNF family), thymic stroma-derived lymphopoietin, mast cell growth factor, stem cell growth factor, epidermal growth factor, growth hormone, tumor necrosis factor, leukemia inhibitory factor, oncostatin M, and hematopoietic factors such as thrombopoietin.

Furthermore, the vectors and DNA constructs of the present invention can be used to create transgenic animals. Transgenic animals can be created by known methods, for example, by the following procedure. First, a gene of interest to be expressed in a transgenic animal is inserted into a DNA construct or vector of the present invention. The vector, or DNA construct, or an expression cassette excised therefrom, is introduced into totipotent cells. As totipotent cells, fertilized eggs, early embryos, embryonic stem cells (ES cells), and such can be used. The introduction into totipotent cells can be achieved by conventional methods, including methods using electrostatic pulse, liposome method, calcium phosphate method, microinjection, or retroviral infection. The totipotent cells treated as described above are transferred into the oviduct of foster mothers to give birth to offsprings. Animals having the gene of interest are selected from the offsprings. Whether animals carry the gene of interest can be determined by Southern blotting or PCR using primers specific to the gene of interest.

The transgenic animals are not limited to particular animal species as long as they are non-human animals, and include mammals such as mice, rats, hamsters, guinea pigs, rabbits, pigs, miniature pigs, cattle, sheep, cats, and dogs; birds such as chicken; fishes; insects; and nematodes. Rodents are preferred for the convenience of manipulation, and mice are particularly preferred.

The vectors and DNA constructs of the present invention can also be used, for example, in antisense methods, and for RNAi. The term "antisense methods" refers to methods for inhibiting translation and transcription and suppressing the expression of a target gene through base pairing of target genes (such as target mRNAs and target DNAs) with antisense oligonucleotides (such as antisense DNAs and antisense RNAs), when the oligonucleotides comprise a sequence complementary to the target gene and exist in cells. Thus, the expression of target DNAs in cells can be inhibited by: inserting antisense oligonucleotides into the DNA constructs or vectors of the present invention; and transforming cells with the DNA constructs or vectors.

Alternatively, target genes can be inhibited by RNA interference (RNAi). The term "RNAi" refers to a phenomenon in which the expression of proteins is inhibited through specific degradation of the intracellular mRNAs corresponding to sequences of double-stranded RNAs (dsRNAs) introduced into cells. Double-stranded RNAs are used in general to achieve RNAi, but it is also possible to use double strands formed in self-complementary single-stranded RNAs. The double-stranded region may cover the whole length, or a portion of RNAs may be single-stranded (for example, one or both ends). Oligo RNAs used in RNAi are often 10- to 100-bp RNAs, and typically 19- to 23-bp RNAs. Thus, the intracellular expression of target genes can be inhibited by: inserting a gene designed to generate double-stranded RNAs in cells into the DNA constructs or vectors of the present invention; and transforming the cells with the DNA constructs or vectors. RNAi can be achieved according to the methods described in: Nature, Vol. 391, p. 806, 1998; Proc. Natl. Acad. Sci. USA, Vol. 95, p. 15502, 1998; Nature, Vol. 395, p. 854, 1998; Proc. Natl. Acad. Sci. USA, Vol. 96, p. 5049, 1999; Cell, Vol. 95, p. 1017, 1998; Proc. Natl. Acad. Sci. USA, Vol. 96, p. 1451, 1999; Proc. Natl. Acad. Sci. USA, Vol. 95, p. 13959, 1998; Nature Cell Biol., Vol. 2, p. 70, 2000; and others.

Furthermore, the vectors and DNA constructs of the present invention can be used in gene therapy. Gene therapy refers to methods for treating diseases by complementing mutant genes, in which the methods comprise introducing external normal genes into patient's cells to alter cell phenotypes. Gene therapies are considered to be effective for not only genetic diseases but also other diseases such as AIDS and cancers, and are categorized into two types of methods: those comprising direct introduction of a gene into the living body to integrate the gene into cells (in-vivo method); and those comprising cell collection from patients, introduction of a gene into the collected cells ex vivo, and transplantation of the cells to the patient (ex-vivo method).

There is no limitation on the type of methods for introducing genes. The introduction can be achieved by microinjection, calcium phosphate method, electroporation, particle gun, methods using viral vectors such as retrovirus, or such. To date, viral vectors are used widely in gene therapy. Viruses used as viral vectors include adenovirus, adeno-associated virus, herpes virus, vaccinia virus, retrovirus, polyoma virus, papilloma virus, and lentivirus.

Some methods for directly introducing genes, such as the particle gun method, are also available. When genes are introduced by in-vivo methods, there is no limitation on the route of introduction. The genes may be introduced through any route, for example, intravenously, intramuscularly, subcutaneously, intracutaneously, or intramucosally, or directly into an organ such as heart or liver. As described above, gene therapy can be carried out by: inserting into a DNA construct or vector of the present invention a gene to be introduced into patient's cells; and introducing the DNA construct or vector into patient's cells by an in-vivo or ex-vivo method. Specific methods of gene therapy can be conducted with reference to Idenshi Chiryo no Kiso Gijutsu (Fundamental techniques of gene therapy), Jikken Igaku (Experimental Medicine) suppl. (Yodosha); Idenshi Dounyu to Hatsugenkaiseki Jikken Hou (Gene introduction and experimental methods for expression analysis), Jikken Igaku (Experimental Medicine) suppl. (Yodosha); Idenshi Chiryo Kaihatsu Kenkyu Handbook (Handbook of gene therapy development research), Ed., The Japan Society of Gene Therapy (NTS), and such.

Furthermore, the vectors and DNA constructs of the present invention can also be used to express DNA vaccines. DNA vaccination is divided into two types of methods: those comprising expression of an antigen DNA in vivo and induction of immune response to the antigen; and those comprising inoculation of a CpG repeat sequence as an immunopotentiator. When a DNA vaccine is inoculated, antigen protein is synthesized in vivo inducing an immune response similar to that resulting from a spontaneous infection by, for example, viruses. The vectors, introduction methods, and introduction routes which are used to express DNA vaccines may be the same as those used in gene therapy.

Furthermore, the vectors and DNA constructs of the present invention can also be used as immunogens to prepare antibodies (J. Virol., Vol. 70(9), p. 6119-25, 1996). In this method, DNA constructs or vectors of the present invention are constructed to express proteins or peptides as the immunogens. The vectors or DNA constructs are then administered into animals to be immunized. Thereby, the immunogens—the proteins or peptides—are expressed in the body of the animals, and antibodies against the proteins or peptides are produced. More specifically, such antibodies can be prepared, for example, by the following method.

First, a gene encoding a protein or peptide that is used as an immunogen is inserted into a DNA construct or vector of the present invention. The DNA construct or vector is administered into animals to be immunized (non-human animals). The administration may be achieved by any method, which includes not only methods comprising direct administration of the vector, but also, for example, electroporation, particle gun method, and methods using a viral vector such as retrovirus. Alternatively, the DNA constructs or vectors may be administered in combination with other substances such as chemical substances (bupivacaine and such). The administration can be achieved by any route, for example, intravenous, intramuscular, subcutaneous, intracutaneous, or intramucosal administration, or direct administration into an organ such as heart and liver. There is no limitation on the species of mammals to be immunized with the sensitized antigens. However, it is preferable to select the mammals considering the compatibility with parental cells used for cell fusion. Rodents, for example, mice, rats, and hamsters; rabbits; and monkeys are used in general. The mammals are immunized as described above, and elevation of desired antibody titer in sera is confirmed. Immune cells are then collected from the mammals and subjected to cell fusion. Particularly preferred immune cells are spleen cells.

Mammalian myeloma cells are used as the other parental cell to be fused with the above-described immune cells. Various known cell lines are preferably used as the myeloma cells, for example, P3 (P3x63Ag8.653) (J. Immunol., Vol. 123, p. 1548-1550, 1979), P3x63Ag8U.1 (Current Topics in Microbiology and Immunology, Vol. 81, p. 1-7, 1978), NS-1 (Eur. J. Immunol., Vol. 6, p. 511-519, 1976), MPC-11 (Cell, Vol. 8, p. 405-415, 1976), SP2/0 (Nature, Vol. 276, p. 269-270, 1978), FO (J. Immunol. Methods, Vol. 35, p. 1-21, 1980), S194 (Trowbridge, I. S. J. Exp. Med., Vol. 148, p. 313-323, 1978), and R210 (Nature, Vol. 277, p. 131-133, 1979). Basically, the cell fusion between the above-described immune cell and myeloma cell can be achieved according to known methods, for example, the method of Kohler and Milstein (Methods Enzymol., Vol. 73, p. 3-46, 1981). More specifically, the above-mentioned cell fusion can be performed, for example, in a conventional nutrient culture medium in the presence of a cell fusion enhancing agent. The cell fusion enhancing agents include, for example, polyethylene glycol (PEG) and Sendai virus (HVJ). If required, adjuvants such as dimethylsulfoxide may also be added to increase fusion efficiency.

The immune cell and myeloma cell ratio can be arbitrarily determined. The preferred ratio of myeloma cells to immune cells is, for example, in the range of 1:1 to 1:10. The culture media used in the above-described cell fusion include, for example, RPMI1640 and MEM that are suitable for the growth of the above-mentioned myeloma cell lines; and other media commonly used for culturing such cells. Furthermore, supplemental sera such as fetal calf serum (FCS) may be used in combination. For cell fusion, predetermined amounts of above-described immune cells and myeloma cells are mixed well in a culture medium described above. A PEG solution (for example, with an average molecular weight of about 1000 to 6000) prewarmed to about 37° C. is then added and mixed at a concentration of typically 30% to 60% (w/v) to yield desired fused cells (hybridomas). Then, an appropriate culture medium is successively added to the cells, and the resulting suspension is centrifuged to remove the supernatant. These processes are repeated to remove the cell fusion agents and such that are unfavorable for hybridoma growth.

Hybridomas prepared by the procedure described above can be selected by culturing in a conventional selection medium, for example, the HAT medium (culture medium containing hypoxanthine, aminopterin, and thymidine). The culture in the HAT medium described above should be continued for a period sufficient to kill cells (unfused cells) other than the hybridomas of interest (typically, for several days to several weeks). Then, screening for hybridomas producing antibodies of interest and single cloning are performed using the conventional limiting dilution method.

Desired human antibodies can be obtained using the hybridomas described above obtained by immunizing non-human animals with an antigen. In addition, desired human antibodies having binding activity can be obtained by sensitizing human lymphocytes in vitro; and fusing the sensitized lymphocytes with human myeloma cells having permanent cell division ability (see, Japanese Patent Application Kokoku Publication No. (JP-B) H1-59878 (examined, approved Japanese patent application published for opposition)). Furthermore, human antibodies against an antigen may be prepared from immortalized antibody-producing cells that are prepared by administering the antigen to a transgenic animal having the whole repertoire of human antibody genes (see, International Patent Applications WO 94/25585, WO 93/12227, WO 92/03918, and WO 94/02602). Such hybridomas producing monoclonal antibodies, which are prepared by the procedure described above, can be subcultured in a conventional culture medium, and stored in liquid nitrogen for a long time. Methods for preparing monoclonal antibodies from the hybridomas include: the method which comprises culturing the hybridomas by conventional methods and preparing antibodies as culture supernatants; and the method which comprises transplanting the hybridomas in compatible mammals, allowing the hybridomas to grow, and preparing antibodies as ascites. The former method is suitable for preparing high purity antibodies, while the latter is suitable for large-scale antibody production.

In the present invention, as monoclonal antibodies, recombinant monoclonal antibodies prepared by cloning antibody genes from hybridomas, inserting the genes into appropriate vectors, introducing the resulting constructs into host, and producing the recombinant monoclonal antibodies by genetic engineering can be used (see, for example, Eur. J. Biochem., Vol. 192, p. 767-775, 1990).

Specifically, mRNA encoding an antibody variable (V) region is isolated from hybridomas producing the antibodies. The isolation of mRNAs can be achieved by preparing total RNAs using known methods, for example, guanidine-ultracentrifugation method (Biochemistry, Vol. 18, p. 5294-5299, 1979) and AGPC method (Anal. Biochem., Vol. 162, p. 156-159, 1987), and preparing the mRNAs of interest using mRNA Purification Kit (Pharmacia) or such. Alternatively, mRNAs can be directly prepared by QuickPrep mRNA Purification Kit (Pharmacia). From the prepared mRNAs, cDNA for the antibody V region is synthesized using reverse transcriptase. cDNA synthesis is achieved using AMV Reverse Transcriptase First-strand cDNA Synthesis Kit (Seikagaku Co.) or such. Alternatively, cDNA synthesis and amplification can be achieved using 5'-Ampli FINDER RACE Kit (Clontech), PCR-based 5'-RACE method (Proc. Natl. Acad. Sci. USA, Vol. 85, p. 8998-9002, 1988, Nucleic Acids Res., Vol. 17, p. 2919-2932, 1989), and such. DNA fragments of interest are purified from the resulting PCR products, and ligated with vector DNAs. The recombinant vectors are prepared by this procedure, and introduced into E. coli or such. After colony selection, the desired recombinant vectors are prepared. The nucleotide sequences of DNAs of interest are then determined by known methods, for example, dideoxynucleotide chain termination method. A DNA encoding the antibody V region of interest is obtained, and then inserted into an expression vector comprising a DNA encoding a desired antibody constant region (C region).

To produce antibodies, in general the antibody genes are inserted into expression vectors so that the genes are expressed under the control of an expression regulatory region, for example, an enhancer or promoter. Then, host cells are transformed with the resulting expression vector, and the antibody expressed. The expression of antibody gene may be achieved by inserting a DNA encoding an antibody heavy chain (H chain) or light chain (L chain) independently into expression vectors and co-transfecting them into host cells, or by inserting DNAs encoding H and L chains into a single expression vector and transfecting the construct into host cells (see, WO 94/11523).

As described above, DNA constructs and vectors of the present invention are applicable in, for example, desired protein production, antisense method, RNAi method, gene therapy, and preparation of DNA vaccines, transgenic animals, and antibodies.

Furthermore, the present invention relates to methods for expressing a desired DNA in host cells, which comprise introducing the vector of the present invention into host cells derived from the same animal order as that from which the β-actin promoter in the vector is derived.

Animal "order" refers to a basic rank that is placed immediately under "class" and above "family", or a taxon at the rank, in the hierarchical Linnaean classification system for organisms. Specifically, animal orders include, for example, Rodentia, Lagomorpha, Macroscelidea, and Scandentia. Preferred is Rodentia. Rodentia includes hamsters, rats, mice, guinea pigs, squirrels, beavers, etc. The expression level of a desired gene can be increased by using a β-actin promoter derived from the same animal order as that from which the host cell is derived.

The present invention also relates to methods for expressing desired DNAs in host cells, which comprise introducing a vector of the present invention into host cells derived from the same animal species as that from which the β-actin promoter in the vector is derived.

The phrase "derived from the same animal species" means that human β-actin promoter is used when the host cell is a human cell; mouse β-actin promoter is used when the host cell is a mouse cell; and hamster β-actin promoter is used when the host cell is a hamster cell. The expression level of a desired gene can be increased by this method using a β-actin promoter derived from the same species as that from which the host cell is derived.

The present invention also relates to methods for increasing the expression level of desired genes, in which a β-actin promoter derived from the same animal order as that from which the host cell is derived is used. The definition of "animal order" is as above. The expression level of a desired gene can be increased by using a β-actin promoter derived from the same animal order as that from which the host cell is derived.

The present invention also relates to methods for increasing the expression level of desired genes, in which a β-actin promoter derived from the same animal species as that from which the host cell is derived is used. The definition of the phrase "derived from the same animal species" is as above. The expression level of a desired gene can be increased by using a β-actin promoter derived from the same animal species as that from which the host cell is derived.

Furthermore, in the present invention, transactivators may be used to increase the expression level of a desired DNA. A vector comprising a DNA encoding such a transactivator may be introduced into host cells so as to express the transactivator during cultivation; the transactivator may alternatively be added to the culture medium. A DNA encoding the transactivator and a DNA encoding the desired protein may be inserted into the same vector. Alternatively, the two DNAs may be inserted separately into different vectors and the resulting vectors may be co-introduced into cells.

All prior-art documents cited herein are incorporated by reference.

EXAMPLES

Hereinbelow, the present invention will be specifically described with reference to Examples, but it is not to be construed as being limited thereto.

Example 1

Construction of Expression Vector pmAct-Luc-neo (1) Cloning of Mouse β-Actin Promoter Sequence information on mouse .beta.-actin was obtained from the mouse genome information disclosed by NCBI (ncbi.nlm.nih.gov/) and the Jackson laboratory (jax.org/). The primers comprising the following sequences were synthesized (Espec oligo service Co.): mAct5-F1 (5'-GGGAGT-GACTCTCTGTCCATTCAATCC-3'/SEQ ID NO: 9) and mAcr5-R1 (5'-TTGTCGACGACCAGCGCAGC-GATATCG-3'/SEQ ID NO: 10). The promoter region (1,577 bp) of mouse .beta.-actin was amplified by PCR. PCR was carried out using TaKaRa LA Taq with GC Buffer (cat. RR02AG) from Takara Bio as reagent and Mouse Genomic DNA (cat. 6650-1) from Clontech as template DNA.

The composition of PCR reaction mixture was:
1.0 µl of template DNA (100 ng/ml);
25.0 µl of 2× GC buffer I;
8.0 µl of dNTP Mixture;
2.0 µl of mAct5-F1 (10 µM);
2.0 µl of mAcr5-R1 (10 µM);
11.5 µl of H$_2$O; and
0.5 µl of LA Taq (5 U/µl).

PCR was carried out under the conditions of:
95° C. for 1 minute;
35 cycles of 95° C. for 30 seconds, 60° C. for 30 seconds, and 72° C. for 90 seconds; and
72° C. for 7 minutes to terminate the reaction.

PCR was carried out using Gene Amp PCR System 2400 (Applied Biosystems). After the PCR product was electrophoresed in a 1% agarose gel, a band corresponding to 1,577 bp was excised and purified with Mag Extractor (Toyobo; cat. NPK-601). The yielded DNA was cloned into pGEM-T-Easy vector (Promega; cat. A1360) and the nucleotide sequence was confirmed by sequencing. The 5' region of the cloned mouse β-actin is shown in SEQ ID NO: 1.

The sequence shown in the public database contains 13 consecutive thymines that start from nucleotide 305, while the cloned region contains 14 consecutive thymines as seen in the sequence shown herein. Thus, the sequence is different from that shown in the database. However, the clone was used in the experiments without altering the sequence. Both "CAAT" starting from nucleotide 414 and "TATAA" starting from nucleotide 475 in the above-described sequence are sequences often found in promoter regions of house keeping genes; thus the obtained region is predicted to be the promoter region of mouse β-actin.

Since the cloned region included the start codon ("ATG" starting from nucleotide 1543 in the above-described sequence) of mouse β-actin, the region of interest (nucleotides 1 to 1542/SEQ ID NO: 2) was amplified by PCR again, using the primers mAct5-BG (5'-AGATCTGGGAGT-GACTCTCTGTCCAT-3'/SEQ ID NO: 11; comprising a BglII site) and mAct5-HN (5'-AAGCTTGGCGAACTAT-CAAGACACAA-3'/SEQ ID NO: 12, comprising a HindIII site) which were synthesized (Espec oligo service Co.) to introduce BglII (5' end) and HindIII (3' end) sites into the region of interest for the convenience of subsequent vector construction.

The composition of PCR reaction mixture was
1.0 μl of template DNA (about 10 ng/ml);
25.0 μl of 2× GC buffer I;
8.0 μl of dNTP Mixture;
1.0 μl of mAct5-HN (10 μM);
1.0 μl of mAct5-BG (10 μM);
13.5 μl of H$_2$O; and
0.5 μl of LA Taq (5 U/μl).

The PCR was carried out under the conditions of:
95° C. for 30 seconds;
30 cycles of 95° C. for 30 seconds, 60° C. for 30 seconds, and 72° C. for 60 seconds; and
72° C. for 7 minutes to terminate.

PCR was carried out using Gene Amp PCR System 2400 (Applied Biosystems). As described above, the amplified PCR product was cloned into pGEM-T-Easy vector and the sequence was determined. The mouse β-actin fragment thus prepared was inserted into BglII-HindIII site of pGL3-Basic (Promega; cat. E1751). Then, the NotI site at nucleotide 4650 in the vector sequence of pGL3-Basic was converted to BamHI site, and the vector backbone spanning from the BamHI site at nucleotide 2004 in the sequence to nucleotide 4650 was converted to the vector backbone (BamHI-BamHI fragment) of pCXN vector to introduce the neomycin-resistant gene, resulting in pmAct-Luc-neo (FIG. 1). The vector resulting from the conversion of the vector backbone of pGL3-Basic is hereinafter referred to as pGLN vector.

(2) Cloning of WPRE and Construction of pmAct-WPRE-Luc-neo

The posttranscriptional regulatory region (WPRE) of 592 nucleotides from 1093 to 1684 in the genomic sequence of Woodchuck hepatitis virus (GenBank Accession No. J04514) was amplified using Assemble PCR and cloned as described below. PCR was carried out using TaKaRa Ex Taq (cat. RR001B) from Takara Bio under the two conditions described below.

<PCR Reaction 1>
The composition of reaction mixture was as follows:
6.0 μl of synthetic DNAs (WP-1 to WP-6; 10 μM and 1 μl each);
5.0 μl of 10× Ex Taq buffer;
8.0 μl of dNTP Mixture;
28.5 μl of H$_2$O; and
0.5 μl of Ex Taq (5 U/μl).

First, PCR was carried out under the reaction conditions of:
94° C. for 5 minutes; and
2 cycles of 94° C. for 2 minutes, 55° C. for 2 minutes, and 72° C. for 2 minutes.

Further, 1.0 μl each of primers WP-f (10 μM and WP-r2 (10 μM) were added to the reaction mixture to adjust the total volume to 50.0 μl. PCR was carried out again under the reaction conditions of:
30 cycles of 94° C. for 30 seconds, 55° C. for 30 seconds, and 72° C. for 1 minute; and
72° C. for 5 minutes.

<PCR Reaction 2>
The composition of reaction mixture was as follows:
13.0 μl of synthetic DNAs (WP-5 to WP-17; 10 μM and 1 μl each);
5.0 μl of 10× Ex Taq buffer;
8.0 μl of dNTP Mixture;
21.5 μl of H$_2$O; and
0.5 μl of Ex Taq (5 U/μl).

First, PCR was carried out under the reaction conditions of:
94° C. for 5 minutes; and
2 cycles of 94° C. for 2 minutes, 55° C. for 2 minutes, and 72° C. for 2 minutes.

Further, 1.0 μL each of primers WP-f2 (10 μM) and WP-r (10 μM) were added to the reaction mixture to adjust the total volume to 50.0 μl. PCR was carried out again under the reaction conditions of:
30 cycles of 94° C. for 30 seconds, 55° C. for 30 seconds, and 72° C. for 1 minute; and
72° C. for 5 minutes.

PCR was carried out using Gene Amp PCR System 2400 (Applied Biosystems). After the amplified PCR product was electrophoresed in a 1% agarose gel, bands of about 200 bp and about 400 bp were excised in reactions 1 and 2, respectively. The DNAs were purified using QIAquick Gel Extraction Kit (QIAGEN; cat. 28704).

PCR was further carried out using each reaction product. TaKaRa Ex Taq (cat. RR001B) from Takara Bio was used as the reagent.

The composition of reaction mixture was as follows:
1.0 μl of the product of reaction 1;
1.0 μl of the product of reaction 2;
5.0 μl of 10× Ex Taq buffer;
8.0 μl of dNTP Mixture;
1.0 μl of WP-f (10 μM);
1.0 μl of WP-r (10 μM);
32.5 μl of H$_2$O; and
0.5 μl of Ex Taq (5 U/μl).

PCR was carried out under the reaction conditions of:
94° C. for 30 seconds;
5 cycles of 94° C. for 15 seconds and 72° C. for 2 minutes;
5 cycles of 94° C. for 15 seconds and 70° C. for 2 minutes;
28 cycles of 94° C. for 15 seconds and 68° C. for 2 minutes; and
72° C. for 5 minutes.

After the amplified PCR product was electrophoresed in a 1% agarose gel, a band of about 600 bp was excised and the DNA was purified using QIAquick Gel Extraction Kit (QIAGEN; cat. 28704). The reaction product was cloned into pGEM-T-Easy vector (Promega; cat. A1360) and the nucleotide sequence was determined. The sequence was confirmed to be identical to that from nucleotide 1093 to 1684 in the sequence of GenBank Accession No. J04514. pGEM-T/WPRE was digested with XbaI, and the resulting WPRE fragment was inserted into the XbaI site of pmAct-Luc-neo to give pmAct-WPRE-Luc-neo. The cloned WPRE sequence is shown in SEQ ID NO: 3, and the synthetic DNAs (SEQ ID NOs: 13 to 33) are shown below.

<Synthetic DNAs used>
WP-1:
(SEQ ID NO: 13)
AATGAACCTCTGGATTACAAAATTTGTGAAAGATTGACTGGTATTCTTAA

WP-2:
(SEQ ID NO: 14)
GCGTATCCACATAGCGTAAAAGGAGCAACATAGTTAAGAATACCAGTCAA

WP-3:
(SEQ ID NO: 15)
ACGCTATGTGGATACGCTGCTTTAATGCCTTTGTATCATGCTATTGCTTC

-continued

WP-4:
(SEQ ID NO: 16)
TTATACAAGGAGGAGAAAATGAAAGCCATACGGGAAGCAATAGCATGATA

WP-5:
(SEQ ID NO: 17)
TTTCTCCTCCTTGTATAAATCCTGGTTGCTGTCTCTTTATGAGGAGTTGTG

WP-6:
(SEQ ID NO: 18)
GTGCACAGCACGCCACGTTGCCTGACAACGGGCCACAACTGCTCATAAAG

WP-7:
(SEQ ID NO: 19)
CGTGGCGTGGTGTGCACTGTGTTTGCTGACGCAACCCCCACTGGTTGGGG

WP-8:
(SEQ ID NO: 20)
GTCCCGGAAAGGAGCTGACAGGTGGTGGCAATGCCCCAACCAGTGGGGGT

WP-9:
(SEQ ID NO: 21)
CAGCTCCTTTCCGGGACTTTCGCTTTCCCCCTCCCTATTGCCACGGCGGA

WP-10:
(SEQ ID NO: 22)
TGTCCAGCAGCGGGCAAGGCAGGCGGCGATGAGTTCCGCCGTGGCAATAG

WP-11:
(SEQ ID NO: 23)
TTGCCCGGTGCTGGACAGGGGCTCGGCTGTTGGGCACTGACAATTCCGTG

WP-12:
(SEQ ID NO: 24)
CCATGGAAAGGACGTCAGCTTCCCCGACAACACCACGGAATTGTCAGTGC

WP-13:
(SEQ ID NO: 25)
TGACGTCCTTTCCATGGGTGCTCGCCTGTGTTGCCACCTGGATTCTGCGC

WP-14:
(SEQ ID NO:26)
GAGGGCCGAAGGGACGTAGCAGAAGGACGTCCCGCGCAGAATCGAGGTGG

WP-15:
(SEQ ID NO: 27)
ACGTCCCTTCGGCCCTCAATCCAGCGGACCTTCCTTCCCGCGGCCTGCTG

WP-16:
(SEQ ID NO: 28)
GAGGGCGAAGGCGAAGACGCGGAAGAGGCCGCAGAGCCGGCAGCAGGCCG
CGGGAAG wp-17:
(SEQ ID NO: 29)
GTCTTCGCCTTCGCCCTCAGACGAGTCGGATCTCCCTTTGGGCCGCCTCC
CCGCCTG

WP-f:
(SEQ ID NO: 30)
TCTAGAAATCAACCTCTGGATTACAAAATT

WP-r:
(SEQ ID NO: 31)
TCTAGAAGGCGGGGAGGCGGCCCAAA

WP-f2:
(SEQ ID NO: 32)
ATCCTGGTTGCTGTCTCTTTATGAG

WP-r2:
(SEQ ID NO: 33)
GTGCACACCACGCCACGTTGCC (3) Construction of phCMV-mAct-Luc-neo The CMV enhancer region (SEQ ID NO: 4) was cloned into the EcoRI site of pmAct-Luc-neo vector to complete phCMV-mAct-Luc-neo (FIG. 1).

(4) Construction of Control Vector

Together with CMV enhancer, human EF1α promoter derived from DHFR-ΔE-RVh-PM1-f (as a reference, WO 92/19759) was inserted into MCS of pGLN vector to construct pCEF-Luc-neo (FIG. 1). In this experiment, all vectors used were purified using EndoFree Plasmid Maxi Kit (cat. 12362) from QIAGEN.

Example 2

Introduction of Vector into CHO Cells and Expression Assay (1) Introduction of Vectors into CHO Cells 2 μg of each vector was mixed with 20 μl of PLUS™ Reagent (Invitrogen; Cat. No. 11514-015), and the total volume was adjusted to 200 μl using OPTI-MEM I Reduced-Serum Medium (Invitrogen; Cat. No. 11058-021). The resulting mixtures were incubated at room temperature for 15 minutes. 20 μl of LipofectAMINE (Invitrogen; Cat. No. 18324-012) and 180 μl of OPTI-MEM I Reduced-Serum Medium were added thereto, and further incubated at room temperature for 15 minutes. CHO cells were prepared to $2 \times 10^4$ cells/well in a 96-well Cell Culture Cluster (Corning; Cat. No. 3595), with 50 μl of OPTI-MEM I Reduced-Serum Medium. 20 μl of the DNA solutions prepared as described above were added to CHO cells. The cells were incubated at 37° C. for 3 hours in a $CO_2$ incubator to introduce the vectors into CHO cells. Then, the culture supernatants were gently removed, and a culture medium for CHO was added. The culture medium used for CHO was prepared by adding 1/100 volume of HT Supplement (100×) liquid (Invitrogen; Cat. No. 11067-030) and 1/100 volume of Penicillin-Streptomycin (Invitrogen; Cat. No. 15140-122) to CHO-S-SFMII medium (Invitrogen; Cat. No. 12052-098). Without further treatment, the cells were incubated at 37° C. for two days in a $CO_2$ incubator.

(2) Luciferase Activity Assay

The luciferase activity was determined using Luciferase Assay System (Promega; Cat. No. E1501). The medium was removed from the cell culture, and 100 μl of 5 times diluted 5× Passive lysis buffer, which was included in the kit, was added to each well. The cells were lysed by shaking. 10-μl aliquots of the cell lysate were transferred to Assay Plate Tissue Culture Treated White with Clear Bottom (Corning; Cat No. 437842). The assay was conducted using MicroLuMAT (Berthold), and the data sampling was carried out using the software WinGlow-Control Program LB96PV ver. 1.24.

Figure 2:
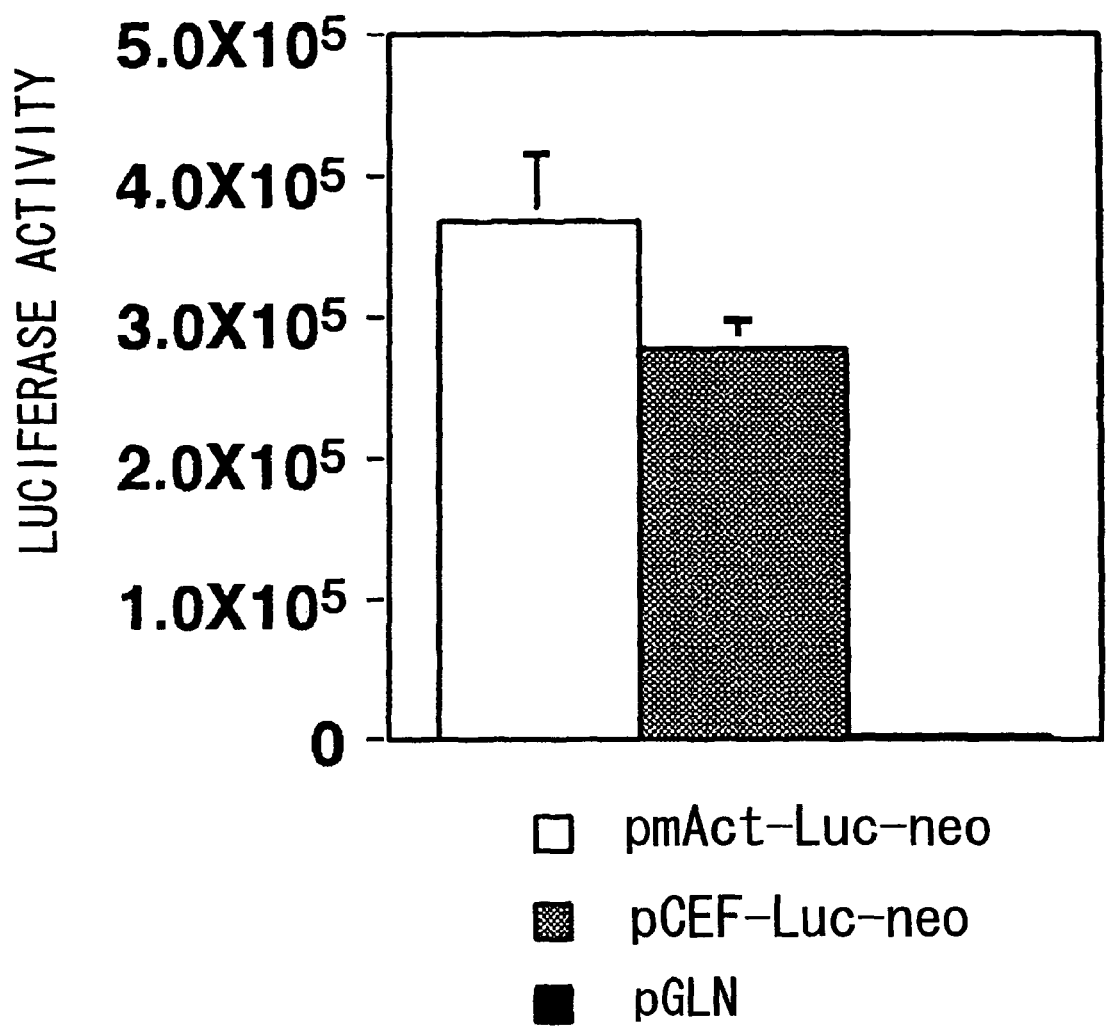
FIG. 2 is a histogram showing a comparison between the existing CEF promoter and the mouse β-actin promoter.
Figure 3:
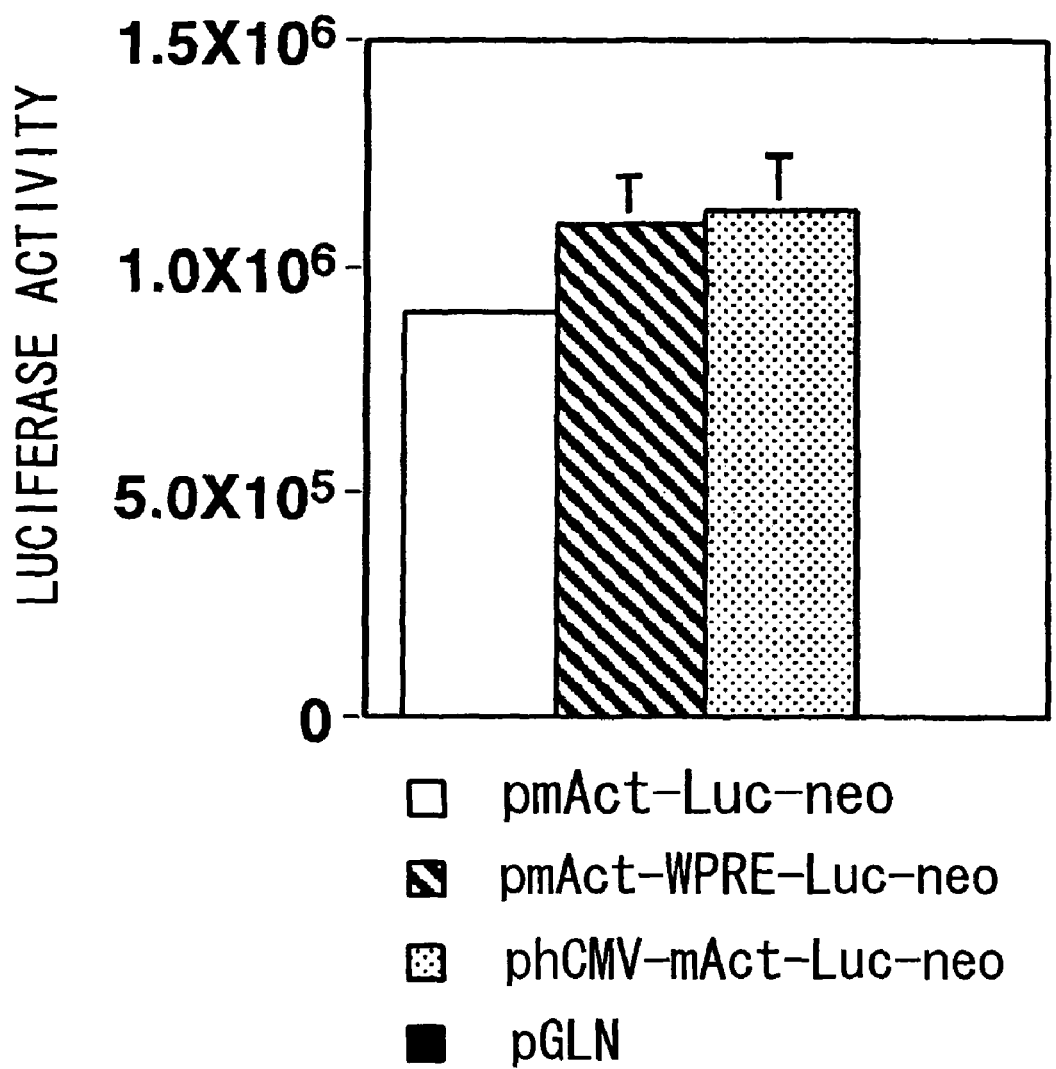
FIG. 3 is a histogram showing the effects of the WPRE and the CMV enhancer on the mouse β-actin promoter.

The assay results obtained by the procedure described above showed that the constructed pmAct-Luc-neo has significantly higher activity than pCEF-Luc-neo ($p < 0.0009$: unpaired t-test) (FIG. 2). This finding shows that the mouse β-actin promoter of the present invention is stronger than the existing CEF promoter. Furthermore, it was also found that the promoter activity of the mouse β-actin is significantly enhanced by attaching WPRE element or CMV enhancer thereto (comparison between pmAct-WPRE-Luc-neo and pmAct-Luc-neo: $p < 0.0005$; comparison between phCMV-mAct-Luc-neo and pmAct-Luc-neo: $p < 0.0007$: unpaired t test) (FIG. 3).

Example 3

Cloning and Alteration of Mouse c-H-ras Gene (1) Cloning of Mouse c-H-ras Gene It has previously been reported that activated human H-Ras enhances the expression efficiency of expression vectors to which human β-actin promoter is inserted (Cytotechnology, Vol. 16, p. 167-178, 1994). However, the effect of activated H-Ras, wild-type H-Ras, or activated K-Ras on the mouse β-actin promoter has not yet been reported. Thus, the effects of mouse H-Ras (active form and wild type) and activated human K-Ras on the mouse β-actin promoter were tested.

The primers mRas-F1 (5'-TCCTGGATTGGCAGCCGCT-GTAGAAGC-3'/SEQ ID NO: 34) and mRas-R1 (5'-GT-TCATCTGGCTAGCTGAGGTCACTGC-3'/SEQ ID NO: 35) were synthesized (Espec oligo service Co.) based on the information of GenBank Accession No. M30733 disclosed at NCBI (ncbi.nlm.nih.gov/). Using the primers, the mouse c-H-ras gene was amplified by PCR. PCR was carried out using TaKaRa LA Taq with GC Buffer from Takara Bio as the reagent, and Embryo Marathon-Ready DNA day 15 (cat. 7459-1) from Clontech as the template cDNA.

The composition of PCR reaction mixture was as follows:
1.0 µl of template DNA;
25.0 µl of 2× GC buffer I;
8.0 µl of dNTP Mixture;
2.0 µl of mRas-F1 (10 µM);
2.0 µl of mRas-R1 (10 µM);
11.5 µl of $H_2O$; and
0.5 µl of LA Taq (5 U/µl).

PCR was carried out under the conditions of:
95° C. for 60 seconds;
35 cycles of 95° C. for 30 seconds, 60° C. for 30 seconds, and 72° C. for 60 seconds; and
72° C. for 7 minutes to terminate the reaction.

PCR was carried out using Gene Amp PCR System 2400 (Applied Biosystems). After the amplified PCR product was electrophoresed in a 1% agarose gel, a band of 660 bp was excised. The DNA was purified using Mag Extractor (Toyobo). The DNA was cloned into pGEM-T-Easy vector (Promega), and the nucleotide sequence was confirmed by sequencing. The determined cDNA sequence of mouse c-H-ras is shown in SEQ ID NO: 5. The nucleotide at position 62 was guanine in the cloned c-H-ras, while it is alanine in the database. Searches of the mouse genome database in NCBI revealed that the nucleotide at this position was guanine. Thus, the clone was used in the experiments without altering the sequence.

(2) Alteration of Mouse c-H-Ras

To efficiently express mouse c-H-Ras in CHO cells, the sequence upstream of the start codon was converted to a sequence that meets the Kozak rule (Nucleic Acids Research, Vol. 15(20), p. 8125-8148, 1987) and the protein non-coding 3'-UTR was removed by PCR using the primers RAS-ATG (5'-GCCACCATGACAGAATACAAGCTT-3'/SEQ ID NO: 36) and RAS-R2 (5'-TCAGGACAGCACACATTTGC-3'/SEQ ID NO: 37). PCR was carried out using the reagent TaKaRa LA Taq (cat. RR002A) from Takara Bio and, as the template, mouse c-H-ras cDNA cloned beforehand into pGEM-T-Easy vector under the following conditions.

The composition of PCR reaction mixture was as follows:
1.0 µl of template DNA;
5.0 µl of 10× LA PCR buffer II ($Mg^{2+}$ free);
5.0 µl of dNTP Mixture;
5.0 µl of $MgCl_2$ (25 mM);
2.0 µl of RAS-ATG (10 µM);
2.0 µl of RAS-R2 (10 µM);
29.5 µl of $H_2O$; and
0.5 µl of LA Taq (5 U/µl).

The PCR was carried out under the conditions of:
95° C. for 60 seconds;
35 cycles of 95° C. for 30 seconds, 60° C. for 30 seconds, and 72° C. for 60 seconds; and
72° C. for 7 minutes to terminate the reaction.

PCR was carried out using Gene Amp PCR System 2400 (Applied Biosystems). After the PCR product was electrophoresed in a 1% agarose gel, a band of 576 bp was excised. The DNA was purified using Mag Extractor (Toyobo). The DNA was cloned into pGEM-T-Easy vector (Promega), and the nucleotide sequence was confirmed by sequencing. The cDNA sequence of altered mouse c-H-ras is shown in SEQ ID NO: 6.

(3) Construction of Activated Mouse H-Ras

A point mutation (the G in the sequence described above was replaced with T) was introduced into the above-described mouse c-H-ras using QuikChange™ Site-Directed Mutagenesis Kit (cat. #200518) from Stratagene. The mutation altered the $12^{th}$ amino acid to valine. Thus, activated H-Ras was obtained.

Primers used were mRasV12-F (5'-GTGGTGGGCGCTG-TAGGCGTGGGAAAG-3'/SEQ ID NO: 38) and mRasV12-R (5'-CTTTCCCACGCCTACAGCGCCCAC-CAC-3'/SEQ ID NO: 39).

The composition of reaction mixture was as follows:
template DNA;
2.0 µl of H-Ras/pGEM-T-Easy (10 ng/µl);
5.0 µl of 10× reaction buffer;
1.0 µl of dNTP Mix;
1.25 µl of mRasV12-F (100 ng/µl);
1.25 µl of mRasV12-R (100 ng/µl);
38.5 µl of $H_2O$; and
1.0 µl of PfuTurbo DNA polymerase (2.5 U/µl).

The PCR was carried out under the conditions of:
95° C. for 30 seconds; and
12 cycles of 95° C. for 30 seconds, 55° C. for 1 minute, and 68° C. for 440 seconds.

PCR was carried out using Gene Amp PCR System 2400. After the amplified PCR product was treated with DpnI according to the manual attached to the kit, E. coli cells were transformed with the product. Plasmid was isolated from the resulting E. coli, and was sequenced to confirm that the mutation had been introduced into the plasmid. The amino acid sequence of activated mouse H-Ras is shown in SEQ ID NO: 7.

Likewise, an activated human K-Ras was also constructed. The amino acid sequence of K-Ras used in the experiments is shown in SEQ ID NO: 8.

Each of these genes was inserted into pCXN vector (Gene, Vol. 108, p. 193-200, 1991) to give pCXN-H-Ras (mouse c-H-ras), pCXN-A-H-Ras (activated mouse c-H-ras), and pCXN-A-K-Ras (activated human K-ras), respectively.

Example 4

Effect of Oncogene Product Ras on the Promoter Activity (1) Introduction of Vectors into CHO Cells 2 µg of vectors to be introduced into CHO cells were prepared by combining two or three types of vectors shown below at various ratios (Table 1). The vectors were introduced into CHO cells by the same method as described in Example 2, and the luciferase activity was determined.

TABLE 1

|  | 10:1 | 100:1 | 1000:1 | 1:0 |
|---|---|---|---|---|
| pmAct-Luc-neo | 1 µg | 1 µg | 1 µg | 1 µg |
| pCXN-H-Ras or pCXN-A-H-Ras or pCXN-A-K-Ras | 0.1 µg | 0.01 µg | 0.001 µg | 0 µg |
| pCXN | 0.9 µg | 0.99 µg | 0.999 µg | 1 µg |
| Total | 2 µg | 2 µg | 2 µg | 2 µg |

Figure 4:
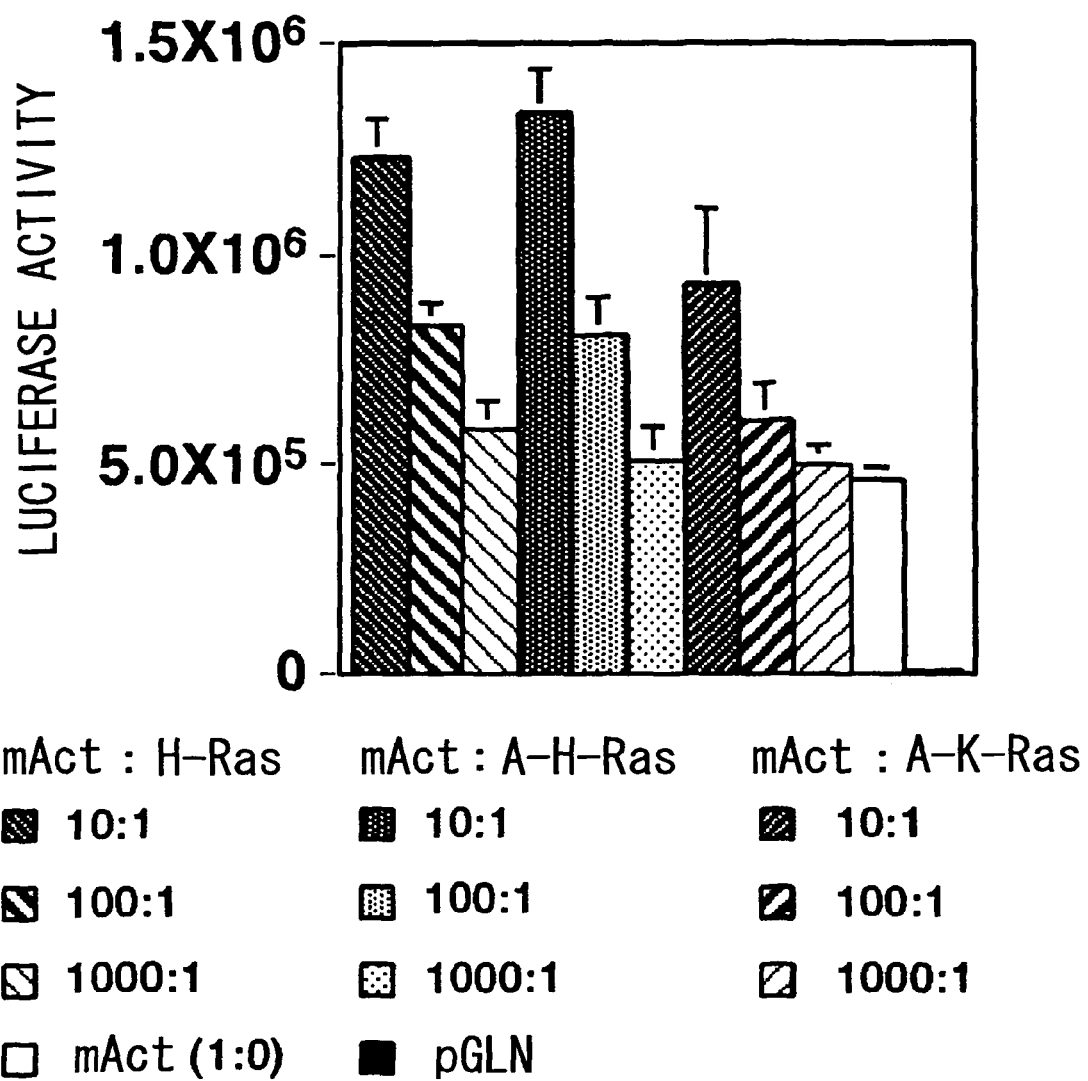
FIG. 4 is a histogram showing the effect of mouse Ras protein on the mouse β-actin promoter.

The result showed that the promoter activity of pmAct-Luc-neo was enhanced in the presence of pCXN-H-Ras (mouse c-H-ras), pCXN-A-H-Ras (activated mouse c-H-ras), or pCXN-A-K-Ras (activated human c-K-ras) (FIG. 4). This finding showed that the oncogene product Ras (whether it is an active form, wild type, H-Ras, or K-Ras) confers stronger activity to the mouse β-actin promoter of the present invention.

INDUSTRIAL APPLICABILITY

Until the present invention, promoters such as the EF1α promoter (WO 92/19759) and CMV promoter were used in vectors to produce proteins in animal cells. In recent years, the biopharmaceutical share in pharmaceuticals has increased. In particular, many antibody pharmaceuticals have been launched onto the market. Antibody pharmaceuticals have to be administered at very high doses as compared to conventional biopharmaceuticals including cytokines such as erythropoietin, G-CSF, or interferons. Thus, the expression of a large amount of protein in animal cells is essential for a stable supply of inexpensive antibody pharmaceuticals. The methods of the present invention enable mass-production of proteins as compared to conventional techniques, and thus are expected to be useful from an industrial viewpoint. The process of immunizing animals with an antigen is required to produce antibody pharmaceuticals. It has been revealed that immunization of animals with a vector itself can be achieved by inserting an antigen gene into such an expression vector. An advantage of the methods of the present invention is that the process of purifying an antigen as a protein can be omitted. It is most important in the immunization process to produce as much antigen as possible in the body of an animal to which a vector is introduced. Thus, the stronger the expression vector, the more preferred it is. While, mouse or rat is used in general to produce monoclonal antibodies, the vectors of the present invention are expected to be suitable for such purposes. Furthermore, the constructs of the present invention are clinically applicable in humans when inserted into gene therapy vectors.

The invention claimed is:

1. A DNA construct comprising a mouse β-actin promoter operably linked to a human Cytomegalovirus (CMV) enhancer.

2. A DNA construct comprising a mouse β-actin promoter operably linked to a CMV enhancer, wherein the CMV enhancer comprises the nucleotide sequence shown in SEQ ID NO: 4 and the mouse β-actin promoter comprises the nucleotide sequence shown in SEQ ID NO: 2.

3. A vector comprising the DNA construct of claim 1.

4. The vector of claim 3, comprising a desired DNA operably linked downstream of the mouse β-actin promoter.

5. The vector of claim 3, comprising and capable of expressing a DNA encoding a transactivator.

6. The vector of claim 5, wherein the transactivator is an oncogene product.

7. The vector of claim 6, wherein the oncogene product is Ras.

8. The vector of claim 4, wherein the desired DNA encodes a desired protein.

9. An isolated cell comprising the vector of claim 4.

10. An isolated cell comprising the vector of claim 4, wherein said cell comprises an activated oncogene.

11. The cell of claim 10, wherein the activated oncogene is on a vector in the cell.

12. The cell of claim 10, which is a transformed cell.

13. The cell of claim 9, which is a mammalian cell.

14. The cell of claim 13, which is a rodent cell.

15. An isolated totipotent cell comprising the vector of claim 4.

16. A method for producing a protein, the method comprising culturing a cell comprising the vector of claim 8 so that the desired protein is expressed, and harvesting the expressed protein from the cultured cell or its medium.

17. The method of claim 16, which comprises adding a transactivator to the medium.

18. A method for expressing a desired DNA in a host cell, which comprises introducing the vector of claim 4 into a host cell derived from the same animal order as that from which the β-actin promoter in the vector is derived; and expressing the desired DNA in the host cell.

19. The method of claim 18, wherein the host cell is a mouse cell.

20. A method for expressing a desired DNA in a host cell, which comprises introducing the vector of claim 4 and a vector comprising and capable of expressing a DNA encoding a transactivator into a mouse host cell; and expressing the desired DNA in the cell.

21. The DNA construct of claim 1, wherein the CMV enhancer comprises the nucleotide sequence shown in SEQ ID NO: 4.

22. The DNA construct of claim 1, wherein the mouse β-actin promoter comprises the nucleotide sequence shown in SEQ ID NO: 2.

23. The DNA construct of claim 1, further comprising a desired DNA operably linked downstream of the mouse β-actin promoter.

24. The DNA construct of claim 2, further comprising a desired DNA operably linked downstream of the mouse β-actin promoter.

25. The DNA construct of claim 21, further comprising a desired DNA operably linked downstream of the mouse β-actin promoter.

26. The DNA construct of claim 22, further comprising a desired DNA operably linked downstream of the mouse β-actin promoter.

27. An isolated cell comprising the DNA construct of claim 1.

28. An isolated cell comprising the DNA construct of claim 2.

29. An isolated cell comprising the DNA construct of claim 21.

30. An isolated cell comprising the DNA construct of claim 22.

31. An isolated cell comprising the DNA construct of claim 23.

32. An isolated cell comprising the DNA construct of claim 24.

33. An isolated cell comprising the DNA construct of claim 25.

34. An isolated cell comprising the DNA construct of claim 26.

* * * * *